United States Patent [19]
Muller et al.

[11] Patent Number: 5,858,410
[45] Date of Patent: Jan. 12, 1999

[54] PHARMACEUTICAL NANOSUSPENSIONS FOR MEDICAMENT ADMINISTRATION AS SYSTEMS WITH INCREASED SATURATION SOLUBILITY AND RATE OF SOLUTION

[75] Inventors: Rainer H. Muller, Berlin; Robert Becker, Biberach; Bernd Kruss, Hochdorf; Katrin Peters, Berlin, all of Germany

[73] Assignee: Medac Gesellschaft Fur Klinische Spezialpraparate, Hamburg, Germany

[21] Appl. No.: 836,305
[22] PCT Filed: Nov. 9, 1995
[86] PCT No.: PCT/EP95/04401
§ 371 Date: Jun. 19, 1997
§ 102(e) Date: Jun. 19, 1997
[87] PCT Pub. No.: WO96/14830
PCT Pub. Date: May 23, 1996

[30] Foreign Application Priority Data

Nov. 11, 1994 [DE] Germany ............... 44 40 337.2

[51] Int. Cl.$^6$ ...................................................... A61K 9/14
[52] U.S. Cl. .................. 424/489; 424/491; 424/493; 424/494; 424/495; 424/499
[58] Field of Search .................. 424/489, 491, 424/493, 494, 495, 499

[56] References Cited

U.S. PATENT DOCUMENTS 4,879,308  11/1989  Alam et al. .
5,145,684   9/1992  Liversidge et al. .............. 424/489

FOREIGN PATENT DOCUMENTS 0 361 928 A3  4/1990  European Pat. Off. ....... A61K 9/107
0 600 528 A1  6/1994  European Pat. Off. ......... A61K 9/14
A 0 600 528   6/1994  European Pat. Off. .

(List continued on next page.)

OTHER PUBLICATIONS

Drug Facts and Compounds, p. 2103 (1994 ed.).
Mueller, "Nanosuspension for the iv administration of poorly soluble drugs stability during sterilization and long term storage", Proc. Int. Symp. Controlled Release Bioactive Mater; Aug. 2, 1995, pp. 574–575.
Bock, "High pressure homogenization of parenteral fat emulsions—influence of process parameters on emulsion quality", European J. Of Pharm. And Biopharm., Jun. 3, 1994, pp. 157–160.
Muller et al. "Nanosuspense For The I.V. Adminstration Of Poorly Soluble Drugs—Stability During Sterilization And Long–Term Storage", Proceed. Intern. Symp. Control. ReL. Bioact. Mater., 22:274–575 (1995).
Brock et al. "High pressure Homogenisation of Parenteral Fat Emulsions—Influence of Process Parameters on Emulsion Quality", Eur. Jnl. Pharm. & Biopharm., 40(3):157–160 (1994).
Sucker et al. Pharmazeutische Technologie, 522, 535 (1978).

Primary Examiner—Thurman K. Page
Assistant Examiner—Brian K. Seidleck
Attorney, Agent, or Firm—Jeffrey S. Melcher; Farkas & Manelli

[57] ABSTRACT

Provided is a drug carrier comprising particles of at least one pure active compound which is insoluble, only sparingly soluble or moderately soluble in water, aqueous media and/or organic solvents, wherein said active ingredient is solid at room temperature and has an average diameter, determined by photon correlation spectroscopy (PCS) of 10 nm to 1,000 nm, the proportion of particles larger than 5 $\mu$m in the total population being less than 0.1% (number distribution determined with a Coulter counter), and, when introduced into water, aqueous media and/or organic solvents, the active compound has an increased saturation solubility and an increased rate of dissolution compared with powders of the active compound prepared using an ultrasonic probe, a ball mill or a pearl mill, the solid particles having been comminuted, without prior conversion into a melt, by using cavitation or shearing and impact forces with introduction of a high amount of energy.

57 Claims, 17 Drawing Sheets

FOREIGN PATENT DOCUMENTS

| | | |
|---|---|---|
| 37 42 473 A1 | 7/1988 | Germany .......................... A61K 9/10 |
| 42 17 842 A1 | 12/1993 | Germany ....................... A61K 31/44 |
| A 42 17 842 | 12/1993 | Germany . |
| 41 40 195 C2 | 10/1994 | Germany .......................... A61K 9/10 |
| 60-258110 (A) | 12/1985 | Japan .............................. A61K 9/10 |
| 60-150221 (A) | 6/1988 | Japan .............................. A61K 9/10 |
| 6-126143 (A) | 5/1994 | Japan ................................ B01F 5/06 |
| WO 90/06746 | 6/1990 | WIPO ........................... A61K 9/107 |
| WO A 90 06746 | 6/1990 | WIPO . |
| WO 93/18752 | 9/1993 | WIPO ........................... A61K 9/127 |
| WO A 93 18752 | 11/1993 | WIPO . |
| WO 94/14426 | 7/1994 | WIPO . |
| WO 94/20072 | 9/1994 | WIPO . |

PHARMACEUTICAL NANOSUSPENSIONS FOR MEDICAMENT ADMINISTRATION AS SYSTEMS WITH INCREASED SATURATION SOLUBILITY AND RATE OF SOLUTION

This application claims benefit of international application PCT/EP95/04401, filed Nov. 9, 1995 published as WO96/14830 May 23, 1996.

1. Field of the Invention

The invention relates to a drug carrier of pure active compound of high saturation solubility and high rate of dissolution, physical stabilization—in particular also using very low surfactant and stabilizer concentrations—and processes and process parameters for its preparation, which produce drug carriers having an average diameter of 10–1,000 nm with simultaneously such a low content of microparticles in the particle population that, in addition to other ways of administration, intravenous injection is also possible.

2. Definition and Advantages of Nanosuspensions

DEFINITION OF THE NANOSUSPENSION IN THE CONTEXT OF THE INVENTION

Disperse system of solid-in-liquid or solid-in-semisolid, the dispersed phase comprising pure active compound or an active compound mixture. The average diameter of the dispersed phase is between 10 nm and 1,000 nm (determined by photon correlation spectroscopy), the distribution of the population being quite narrow, that is to say the proportion of microparticles in the particle population is very low. The nanosuspension can be surfactant-free, but can also comprise surfactants or stabilizers or both. The nanosuspension can also be lyophilized or spray dried, and the nanoparticles of a nanosuspension can also be incorporated into a solid carrier matrix.

ADVANTAGES OF NANOSUSPENSIONS

The preparation of medicament particles having a size in the nanometer range has many advantages from the pharmaceutical technology, biopharmaceutical, pharmacological and medical aspect.

Some of these are:

1. The dissolution rate increases as the particle surface area increases in accordance with the Noyes-Whitney law. As a result, the rate of flooding of active compounds increases, and the maximum plasma level is reached faster (e.g. oral or i.v. administration of a nanosuspension). The preparation of nanosuspensions is therefore of interest for all substances with which the dissolution rate is the determining factor for the bioavailability.

2. Intravenous administration of sparingly soluble active compounds can be rendered possible by nanosuspensions. More and more newly developed medicaments have a very low solubility or are almost insoluble, specifically in water and, at the same time, in organic solvents. Pharmacological testing following oral or i.m. administration is not possible because of the low bioavailability due to the low solubility. Intravenous injection is excluded because of the lack of a suitable solvent mixture. As a nanosuspension, the active compound can be injected without blockade of blood capillaries. In the relatively large volume of blood compared with the injection volume (e.g. 20 ml to 61 ), the active compound then dissolves, the blood proteins often additionally having a solubilizing action.

3. Via formulation as a nanosuspension, a reduction in the injection volume of drugs can be achieved. If the water-solubility is low, the result is a relatively large volume to be administered if an active compound is administered as a solution. Alternatively, the active compound can be formulated as a nanosuspension, the medicament particles being dispersed in a saturated solution of the active compound. Infusion could thus be replaced by a bolus injection.

4. Nanosuspensions can be employed for controlled drug delivery. After oral administration, oral immunization could take place via the M cells in the gastrointestinal tract, and selective concentration in the absorption windows of the gastrointestinal tract could be achieved via bioadhesives.

5. Nanosuspensions are delivery systems for drug targeting. After intravenous injection, particles accumulate specifically in certain organs, e.g. liver, spleen or bone marrow, as a function of their surface properties (R. H. Muller, Colloidal Carriers for Controlled Drug Delivery and Targeting, Wissenschaftliche Verlagsgesellschaft Stuttgart, 1991). After parenteral administration, accumulation in the lymphatic system can be achieved. Targeted accumulation of the active compound at the site of action reduces side effects and increases the therapeutic efficiency and therefore the therapeutic index.

3. State of knowledge of nanosuspensions and preparation technology

It has not yet been possible to utilise the advantages of nanosuspensions, since this particle size range is accessible to only a very limited extent with conventional grinding techniques (dry grinding in ball mills, air jet milling). Although powders with 100% of the particles smaller than approx. 25–50 $\mu$m are obtained by air jet milling, these powders comprise only a proportion of a few per cent of particles in the nanometer range. The particle size distribution, measured with a laser diffractometer (LD), of the drug RMKP 22 (4-[N-2-hydroxy-2-methylpropyl)-ethanolamine]-2,7-bis(cis-2,6-dimethyl-morpholin-4-yl)-6-phenyl-pteridine) which has been ground in an air jet is shown in FIG. 1 by way of example. Although 100% of the particles are smaller than 25 $\mu$m, only 8% of the particles are in the range below 1,000 nm, i.e. 92% are >1 $\mu$m. It could thus be assumed that the nanometer fraction is separated off and the remaining particles are subjected to a renewed grinding process in order thus to obtain further nanoparticles. However, this is possible to only a limited extent, since as the grinding process progresses, ever more perfect crystals arise as the degree of comminution increases, and these are subsequently no longer to be comminuted further by the maximum grinding forces which can be achieved (P. List, Arzneiformenlehre [Drug forms], Wissenschaftliche Verlagsgesellschaft Stuttgart, 1976).

Summarizing, it can thus be said that nanoparticles can be prepared from drugs by conventional dry grinding techniques and subsequent fractionation, but with one great disadvantage: loss of the active compound of approx. more than 90%. Profitability as a rule no longer exists.

Wet grinding has been employed as a further grinding technique (Sandell, E., Grundriss der Galenischen Pharmazie [Principles of galenical pharmacy], Govi-Verlag GmbH, Frankfurt am Main, 1962), for example using a Premier Mill (Sandell, loc. cit.) or a ball or pearl mill (Hagers Handbuch der pharmazeutischen Praxis [Hagers handbook of pharmaceutical practice], Springer-Verlag, Berlin, 1925). Although a main population of particles in the nanometer range results when a pearl mill is used, a significant proportion of particles larger than 1 $\mu$m is still present. FIG. 2 shows the 50%, 90%, 95% and 99% LD diameters from the particle size distribution of the drug RMKP 22. RNXP 22 was ground (Dispermat) in a pearl mill without addition of surfactant (FIG. 2: A) and with addition of 3% Tween 80 (FIG. 2: A+surfactant). The 50% diameter of the surfactant-free sample is already approx. 2 μm, i.e. 50% of the particles are >2 μm. Some of these micrometer particles can be attributed to agglomeration. As described in the literature (Sandell, loc. cit.; P. H. List, Arzneiformenlehre [Drug forms], Wissenschaftliche Verlagsgesellschaft mbH Stuttgart, 1976; Sucker, H., Speiser, P., Fuchs, P., Pharmazeutische Technologie [Pharmaceutical technology], George Thieme Verlag Stuttgart, 1978; Munzel, K., Buchi, J., Schultz, O.-E., Galenisches Praktikum [Practical galenics], Wissenschaftliche Verlagsgesellschaft mbH Stuttgart, 1959), aggregation in suspensions can be prevented by addition of surfactants (Tween 80, Pluronic F 68) or generally stabilizers (e.g. polyvinylpyrrolidone—PVP, Pluronic F 68). After addition of Tween 80 to prevent aggregation, only a slight reduction in the diameters of the volume distribution resulted, which demonstrates the less effective comminution process of a pearl mill per se (FIG. 2). A further reduction in the particle size in such mills is possible if the viscosity of the dispersion medium is increased, but the speed of rotation must remain constant (W. Holley, Dissertation, Friedrichs University Karlsruhe, 1984, W. Holley, Homogenisieren mit Hochdruck, Niederdruck, Ultraschall und anderen Techniken [Homogenization by high pressure, low pressure, ultrasound and other techniques], paper at the 35th Annual Congress of the APV, Strassburg, 1989). As a rule, this is also recommended by manufacturers of mills (e.g. Dyno-Mill, A. Bachoffen AG Maschinenfabrik). Surfactant-stabilized microparticles have also been patented (U.S. Pat. No. 5,246,707), it also being possible for these additionally to comprise iron particles within the microparticles in order to allow location of the particles via magnetic fields.

The preparation of nanosuspensions by wet grinding has been patented by Motoyanna et al. as a process (U.S. Pat. No. 4,540,602) and wet grinding with a pearl mill with addition of substances such as PVP and Pluronic F68 has been patented by Liversidge et al. (U.S. Pat. No. 5,145,684). However, the processes have the following disadvantages:

1. Only batchwise production with a batch size which is too low for industrial manufacture is possible.

2. Abrasion occurs on the grinding beads employed (zirconium dioxide, glass). Zirconium dioxide and abraded glass may seem still tolerable for oral administration, but are less tolerable for parenteral or even intravenous administration.

3. A relatively high proportion of particles >5 μm is still present. Analysis of the batch from FIG. 2 with the Multisizer II Coulter counter, which is more sensitive than a laser diffractometer, gave a figure of 52,671,000 particles per ml of a 5% strength drug suspension which were larger than 5 μm.

Another preparation method which has been known for a long time is "via humida paratum", precipitation by pouring a solution of the active compound into a non-solvent (Hagers Handbuch der pharmazeutischen Praxis [Hagers handbook of pharmaceutical practice], Springer-Verlag, Berlin, 1925). By pouring into the non-solvent, the Ostwald Mie range is rapidly passed through and a very fine precipitate separates out. The particles which have precipitated out likewise have a significant proportion in the micrometer range. FIG. 3 shows the particle size distribution (laser diffractometer, volume distribution) of an RMKP 22 suspension prepared via humida paratum. The drug was dissolved in ethanol (3%, 20 ml) and the solution poured into 100 ml of an aqueous surfactant solution (1.2% Pluronic F68). The end of the measuring range is 80 μm, and a large fraction between approx. 18 μm to 80 μm was detected.

The preparation of nanosuspensions by precipitation has also been patented (EP 0 275,796 and EP 0 418 151 AI (model drug: amphotericin)).

However, precipitation has the following disadvantages:

1. Residual content of solvents in the product, which can be removed only with great difficulty or incompletely.

2. During precipitation, a delay in crystallization of the medicament occurs.

3. Sometimes a quite high proportion of particles in the micrometer range.

Nanosuspensions can also be prepared by high shearing forces in liquids (jet stream) combined with particles colliding with one another: apparatuses for producing streams of liquid with a high speed (e.g. 700 m/s) are the Microfluidizer (Microfluidics Inc.) or the Nanojet (Nanojet Engineering Gmbh), a further development of the Microfluidizer.

DESCRIPTION OF THE INVENTION

Figure 1:
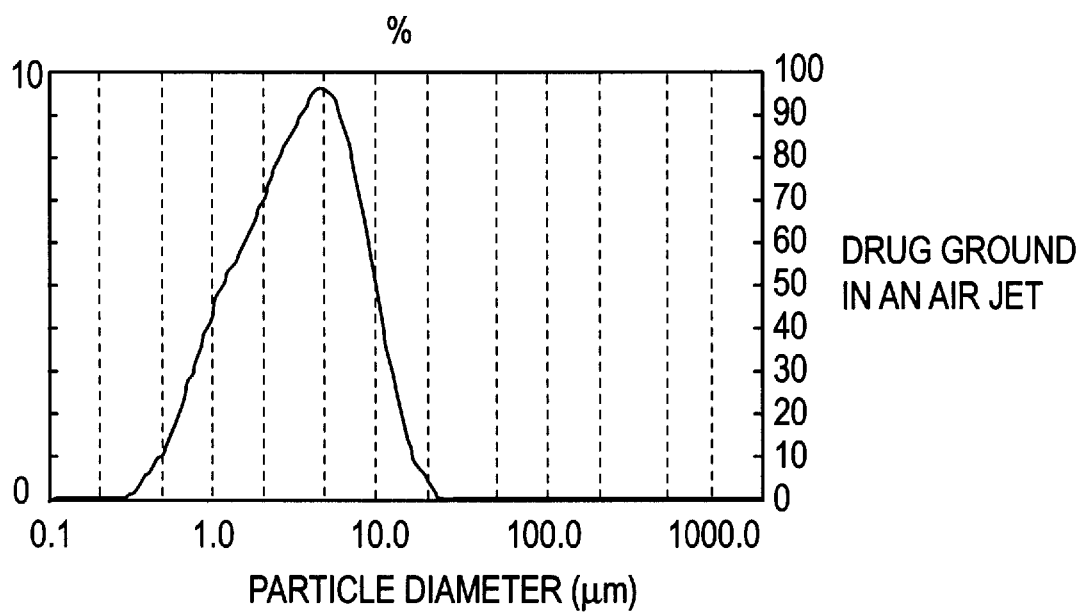
FIG. 1 illustrates the particle size distribution of a conventional drug that has been dry-ground using a ball mill.
Figure 2:
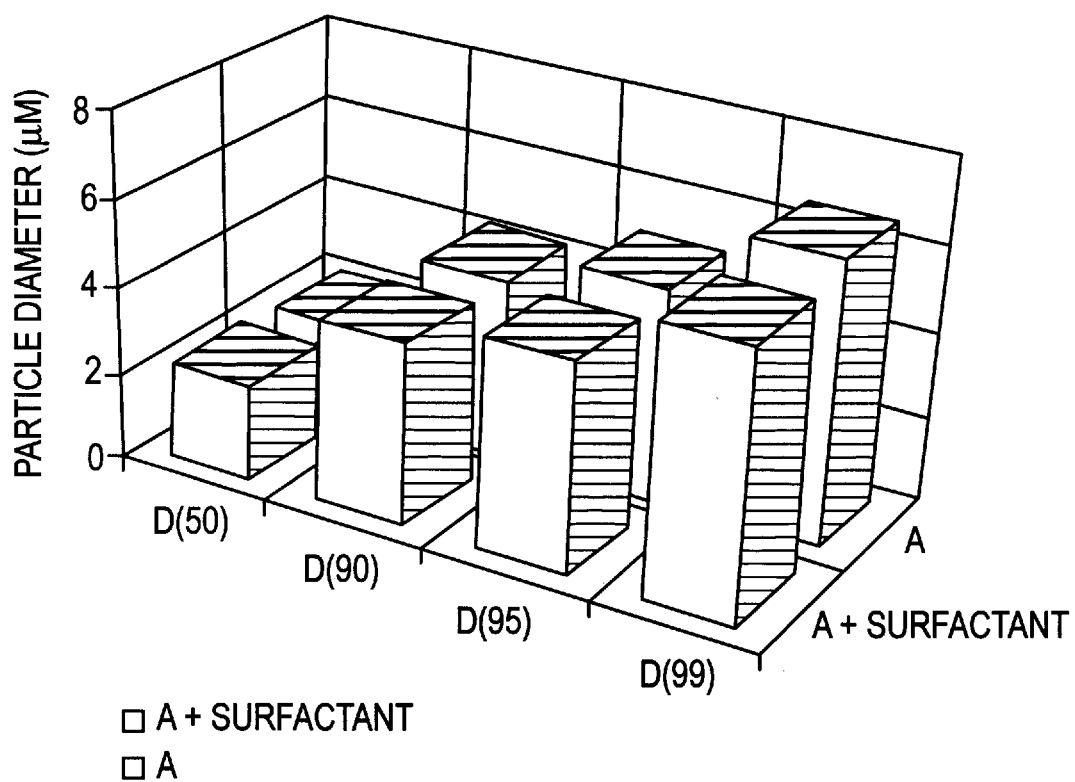
FIG. 2 illustrates the particle size distribution of a conventional drug that has been wet-ground using pearl mill in the presence and absence of a surfactant.
Figure 3:
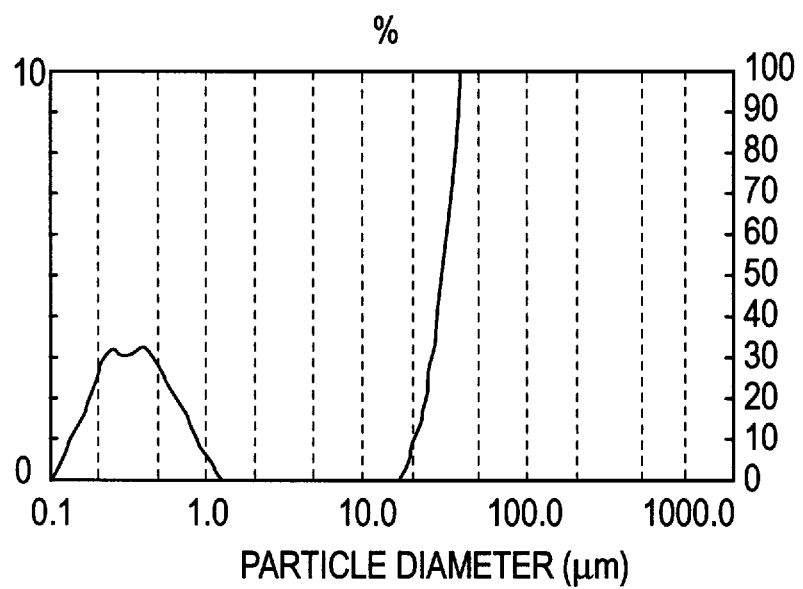
FIG. 3 illustrates the particle size distribution of an RMKP 22 suspension prepared via humida paratum.

The main difficulties in the preparation of nanosuspensions are, inter alia, reduction in the proportion of particles in the micrometer range (especially of particles larger than 5 μm in suspensions for i.v. administration) and the use of a process which both allows large-scale industrial production and at the same time gives a product which can be approved as a medicament by the approval authorities (Bundesgesundheitsamt in the FRG, FDA in the USA) from the toxicological aspect. Piston-gap high-pressure homogenizers have been employed for many years for large-scale industrial production for dispersing oils in the context of production of fat emulsions for parenteral feeding. The dispersing principle is cavitation. In this procedure, a coarsely disperse pre-emulsion is forced through a gap approx. 25 µm wide. As a result, in accordance with Bernoulli's equation (Sucker, H., Speiser, P., Fuchs, P., Pharmazeutische Technologie [Pharmaceutical technology], George Thieme Verlag Stuttgart, 1978), the static pressure exerted on the liquid falls below the vapour pressure of the liquid at the prevailing temperature because of the high flow rate. The liquid boils and the formation of gas bubbles occur, which collapse on exit from the gap under the normal pressure which now prevails (cavitation). As a result of the powerful implosion forces, the oil drops are torn into drops approx. 200 to 500 nm in size. It was considered that this dispersing system is unsuitable for comminution of solids— fed in the form of a coarse suspension—since it was expected that the gap would become blocked by powder particles having a size of up to 50 µm or also by aggregation of smaller particles. It was also dubious whether the implosion forces were sufficient for comminution of crystals with few defects, i.e. very hard crystals.

Suspensions were prepared with a drug, which was ground in an air jet, in an aqueous surfactant solution. The drug concentration was 3%, 9% and 15%. RMKP 22 was employed as the model drug. The suspension was homogenized in a piston-gap homogenizer under conditions of 1,500 bar, three cycles. The diameters of the resulting nanoparticles dropped from the 1st to the 3rd cycle (examples 1 to 3).

The diameter of the main population and the proportion of particles in the micrometer range was investigated as a function of the number of cycles. The diameter of the main population and the proportion of particles in the micrometer range decreased with the number of cycles, a marked drop occurring during the first 3 and 6 cycles, a smaller drop occurring from the 5th or 7th to the 10th cycle, and no further change occurring from the 10th cycle because the dispersity limit under the power density resulting at 1,500 bar had been reached (examples 4 and 5).

Nanosuspensions which were obtained after 10 cycles showed a proportion of particles >1 µm and >5 µm per unit volume which was several times lower than in commercial fat emulsions for parenteral nutrition (example 6). Capillary blockade which occurs with fat emulsions is reversible by metabolism of the fat emulsion. In approx. 4 hours, a fat emulsion administered is broken down by the lipases in the endothelium. In the case of the nanosuspension, a blockade is reversible by dissolution of the nanoparticles. Because of the increased saturation solubility (example 7), a rapid dissolution process of the nanoparticles occurs when the nanosuspension is diluted (example 8).

By reducing the diameter of the microparticles from 3.64 µm (Dm) to the diameter of the nanosuspension of 800 nm (Dn), a marked increase in the saturation solubility occurred. By shaking experiments, a saturation concentration for the RMKP 22 micro-particle suspension of Csm 1.98 mg/l was determined, and for the RMKP 22 nanosuspension a significantly higher Csn of 3.29 mg/l was determined (example 7).

An increase in the saturation solubility by reducing the particle size was indeed expected, but not at this level. An increase in the saturation solubility when the particle size is decreased is postulated in the Ostwald-Freundlich equation (Voigt, R., Lehrbuch der pharmazeutischen Technologie [Textbook of pharmaceutical technology], Verlag Chemie Berlin, 1984), but this does not have an effect on particles in the micrometer range (saturation solubility, as a substance-specific parameter, dependent solely on temperature).

$$\frac{RT}{M} \ln \frac{Csm}{Csn} = \frac{4y}{\sigma} (1/Dn - 1/Dm)$$

R—universal gas constant T—absolute temperature
M—molecular weight
Dm—diameter of microparticles Csm—saturation solubility of microparticles
Dn—diameter of nanoparticles Csn—saturation solubility of nanosuspension
y—surface tension of the σ— density active compound The increase in the saturation solubility which occurred to this level is hard to explain with the relatively low difference in particle size. The only possible variable parameter in the above equation is the surface tension y. According to Ostwald-Freundlich, the increase in saturation solubility observed can be explained only by an unexpected change in the surface tension y, which must take place due to the homogenization process. The energy introduced during the homogenization process must have led to an increase in y and an associated increase in the saturation solubility. It is thus evidently possible, by conversion of the microparticles into nanoparticles by means of a high-energy process, to increase the surface tension to such an extent that as a result the saturation solubility increases greatly. No polymorphism, as a possible cause for the higher saturation solubility, was to be detected. The X-ray diffractogram shows no differences between microparticles and the nanosuspension. Another possible reason is hydrophobization of the surface due to breaking up of "ideal" crystals, which cannot be destroyed by a conventional grinding technique. Broken surfaces are no longer preferentially formed at defects (List, loc. sit.), but pass directly through the crystal. If the broken surfaces newly formed from an ideal crystal have a higher surface tension, a higher saturation solubility results. Another possible effect which is not ruled out is the change in the radius of curvature. The packing density of the surfactants at the surface is no longer optimal due to the changed geometric circumstances, that is to say packing is less dense. This results in an increased surface tension at the interface with the nanoparticles.

From storage data so far over several weeks, this state of a more highly saturated solution is also stable, no particle growth due to recrystallization took place.

The Noyes-Whitney equation describes the rate of dissolution dc/dt (Stricker, H. (editor), Physikalische Pharmazie [Physical pharmacy], Wissenschaftliche Verlagsgesellschaft, Stuttgart 1937):

$$\frac{dc}{dt} = DA \cdot \frac{(Cs - Ct)}{dx}$$

dc/dt—rate of dissolution D—diffusion constant
A—surface area of the Cs—saturation concentration particles
Ct—concentration at time t in the dissolving medium
dx—distance between the saturated layer on the particle surface and the site with Ct From theoretical considerations, an increase in the rate of dissolution by conversion of the microparticles into the nanoparticles had been expected merely on the basis of the increase in the surface area A, which makes up an increase by a factor of 4.55 when a 3.64 μm particle is converted into an 800 nm particle. Because of the increase in the saturation solubility which surprisingly occurred (due to the unexpected significant change in surface tension y), an additional increase in the rate of dissolution occurs. This has the effect of fast dissolution of particles, even in solutions with a concentration of Csm (example 8). For intravenous administration of nanosuspensions, this of course has the advantage that because of the high dilution (e.g. 10 ml in 6 l ) in the blood, rapid dissolution of the injected substance occurs. The proteins present in the blood have the effect of further promoting dissolution via possible solubilization of active compounds. As a highly disperse system, instability during storage of the nanosuspensions cannot be ruled out. The long-term stability was therefore investigated by PCS and laser diffractometry. In nanosuspensions of optimized composition, no particle growth was detected during storage at 4°–8° C. for 8 weeks (example 9).

Studies have been carried out on the sterilizability by autoclaving and also by means of gamma sterilization. The influence of the following parameters on sterilizability was determined:
a. the chemical nature of the surfactant (e.g. lecithins, various phospholipids and, as ethoxylated stabilizers, Tween 80 and Pluronic)
b. mixtures of two or more surfactants
c. the concentration of the surfactants or stabilizers On the basis of theoretical considerations, the surfactant or stabilizer concentration should be significantly above the concentration to reach the plateau of the adsorption isotherms, so that the surfaces of the dispersed particles are covered densely by stabilizing molecules. If the surface cover is inadequate, aggregate formation can occur by means of bridging, anchoring or flocculation due to interaction of hydrophobic surfactant particles (B. W. Müller, P. List, Arzneiformenlehre [Drug forms], in print). It is important to exceed the plateau concentration specifically for steric stabilizers (e.g. ethoxylated block copolymers, such as Pluronic), since the maximum thickness of the adsorption layer is thus achieved (Kayes, J. B. and Rawlins, D. A., Adsorption characteristics of certain polyoxyethylene-polyoxypropylene block copolymers on polystyrene latex, Coll. Polym. Sci. 1979, 257, 622–629). Steric stabilization increases with the layer thickness, a layer thickness of >10 nm being necessary for perfect steric stabilization (Buscall, R. and Ottewill, R. H., The stability of polymer latices in Polymer Colloids, Elsevier Applied Science Publishers, London, 1986, pp. 141–217). It is often advantageous to exceed the plateau concentration considerably, since stabilization by displacement is then possible (B. W. Müller, P. List, Arzneiformenlehre [Drug forms], in print). When two particles approach each other, the surfactants are displaced from the intermediate space and a surfactant-free zone forms between the particles. There is now an osmotic pressure difference between the surfactant-free zone and the surrounding surfactant solution, and surfactant molecules press between the particles on the basis of this difference and push them apart again, and thus prevent the aggregation. Pushing in is more pronounced the greater the osmotic difference, that is to say the higher the surfactant concentration in the dispersion. On the basis of the above considerations, surfactant concentrations in the range from one to several per cent are therefore employed. The standard surfactant concentration in O/W emulsions for parenteral feeding is therefore also 1.2% lecithin (e.g. commercial products such as Intralipid, Lipofundin, Endolipide, Lipovenos etc.). Higher concentrations are also described in the literature as considerably more stabilizing than 0.6%, and are also used (Meyer, C. E., Fander, J. A., Schurr, P. E., Webster, H. D., Metabolismo 6, 591, 1957). For ethoxylated surfactants of the Pluronic type (poloxamer), values in the range from 0.05% to 0.1% are also stated for achieving the plateau of the adsorption isotherms—depending on the poloxamer type (Kayes and Rawlins, loc. cit.; Wesemeyer, H., Dissertation, Christian-Albrechts University Kiel, 1993), so that here also concentrations from 1% upwards are as a rule employed for stabilization, often even in addition to one or more other cosurfactants, which leads to surfactant concentrations in total of up to 5% (Schwarz, C., Mehnert, W., Lucks, J. S., Müller, R. H., Solid lipid nanoparticles for controlled drug delivery. Journal of controlled release, 1994; Westesen, K., Siekmann, B., Submicron-sized parenteral carrier systems based on solid lipids, Pharmaceutical and Pharmacological Letters, Springer-Verlag 1992).

However, sterilization of nanosuspensions stabilized with a varying surfactant concentration surprisingly resulted in the lowest particle growth at a Tween 80 concentration of 0.03% to 0.1%, that is to say in the range of the concentration for reaching the plateau of the adsorption isotherms or also slightly below this (example 12). This means that at very low surfactant and stabilizer concentrations, nanosuspensions are optimum starting suspensions for autoclaving.

Since the lowest possible surfactant content is desirable from the toxicological aspect, surfactant-free nanosuspensions have also been prepared (example 13). The active compound employed was carbamazepine, and to reduce sedimentation during pumping through the homogenizer, sodium carboxymethylcellulose was added to increase the viscosity.

The jet stream was also investigated for its suitability as a dispersing principle. High-quality nanosuspensions were also obtained (example 14). A disadvantage of this principle is that as yet it is still used relatively little in the production plants of the pharmaceuticals industry.

The particle size obtained during dispersion is a function of the power density employed, the hardness of the drug, the viscosity of the dispersion medium (increase in the power density with the viscosity at a constant flow rate of the dispersing phase) and the surfactant properties (e.g. rate of migration of the surfactants to the surfaces newly formed in the dispersing process, stabilizing action of the surfactant on the surface in the dispersing process, i.e. under exposure of the suspension to stress on the basis of the high amount of kinetic energy introduced). The particle size obtained can be influenced by modifying the preparation parameters on the one hand and the formulation composition on the other hand. The preparation parameters and formulation composition for a nanosuspension of very small average diameter are given in example 15.

The fields of use for the medicament carriers according to the invention are diverse. For example, they can be used for parenteral (in particular intravenous administration and for lymphatic absorption), enteral (in particular mucoadhesive drug forms), pulmonary and topical (nasal, dermal, intraocular) drug administration and for administration into body cavities.

Parenteral administration is:
1. Intravenous administration (targeting to the liver, spleen, bone marrow, lung and blood cells, such as lymphocytes, monocytes and granulocytes, generation of particles circulating in the blood with continuous dissolution of the active compound in the blood compartment).

2. Lymphatic absorption of medicament carriers by injection close to lymph vessels (targeting of cytostatics to lymph nodes).
3. Intramuscular administration (depot form for prolonged or sustained release of active compounds, e.g. corticoids. Because of the reduced amount of fluid in the tissue, a retarded dissolving process occurs, above all with sparingly soluble to practically insoluble active compounds).
4. Intraarticular administration (e.g. for antirheumatics and immunosuppressives for arthritis).
5. Intracavital administration (e.g. cytostatics for forms of cancer in the peritoneum and in the pleural cavity)
6. Subcutaneous and intradermal administration (e.g. depot forms for cytostatics for skin cancer).

Enteral administration forms are used, in particular, for:
1. Increasing absorption by the preparation of mucoadhesive drug carriers which increasingly accumulate on the mucosa and also remain there longer.
2. Oral immunization due to interaction of the drug carrier with e.g. M cells in Peyer's patches.
3. Absorption of active compounds via the M cells
4. Increase in the absorption of lipophilic active compounds by non-specific accumulation on the mucosa, e.g. lipophilic vitamins.
5. Absorption of drug carriers into the lymphatic system.

Possible pulmonary administration forms are, in particular:
1. Aerosols, metered aerosols (spraying an aqueous dispersion of the drug carrier)
2. Aerosols, metered aerosols (spraying a powder, where the medicament carriers in the nanometer range have been sprayed onto carrier particles, such as lactose, in the micrometer range. The lactose dissolves in the lung, and releases the medicament carriers, e.g. for the purpose of absorption by macrophages, or e.g. they remain on the surface of the lung, and active compounds with the target group of peritoneal cells I or II dissolve). 3. Instillation of the dispersion, where substances which promote spreading, such as phospholipids or phospholipid-associated proteins, are possibly added.

Examples of topical use:
1. Dermatological medicaments for administration of e.g. corticoids and antimycotics. Due to the increased saturation solubility of the medicament carriers, a higher concentration gradient results than with active compound crystals in the micrometer range, and absorption into the skin is promoted. In addition, because of their small size, the drug carriers have the possibility of entering between the intermediate spaces of the stratum corneum cells (analogously to liposomes), which also promotes absorption into the skin.
2. Ophthalmic suspensions, ophthalmic gels or inserts, e.g. for pilocarpine or beta-blockers. Because of the particulate structure, prolonged residence times occur, as are already described for nanoparticles of polymers. Because of the slow solubility, the inserts have the effect of sustained release without using a control membrane.
3. Cosmetics analogous to liposomal preparations.
4. Particulate administration of active compounds into the nose for the purpose of nasal absorption.

Examples of medicament groups which are to be processed in the form of a nanosuspension are (where appropriate in the form of their sparingly water-soluble form, e.g. as the base instead of the hydrochloride):
1. Analgesics/antirheumatics
   e.g. morphine, codeine, piritramide, fentanyl, levomethadone, tramadol, diclofenac, ibuprofen, indomethacin, naproxen, piroxicam
2. Antiallergics
   e.g. pheniramine, dimethindene, terfenadine, astemizole, loratidine, doxylamine and meclozine
3. Antibiotics/chemotherapeutics
   e.g. rifampicin, ethambutol, thiacetazone,
4. Antiepileptics
   e.g. carbamazepine, clonazepam, mesuximide, phenytoin, valproic acid
5. Antimycotics
   a) internal: e.g. natamycin, amphotericin B, miconazole
   b) external also: e.g. clotrimazole, econazole, fenticonazole, bifonazole, ketoconazole, tolnaftate
6. Corticoids (internal preparations)
   e.g. aldosterone, fludrocortisone, betamethasone, dexamethasone, triamcinolone, fluocortolone, hydroxycortisone, prednisolone, prednylidene, cloprednol, methylprednisolone
7. Dermatics
   a) Antibiotics: e.g. tetracycline, erythromycin, framycetin, tyrothricin, fusidic acid
   b) Virostatics as above, and also: e.g. vidarabine
   c) Corticoids as above, and also: e.g. amcinonide, fluprednidene, alclometasone, clobetasol, diflorasone, halcinonide, fluocinolone, clocortolone, flumethasone, diflucortolone, fludroxycortide, halomethasone, desoximetasone, fluocinolide, fluocortin butyl, fluprednidene, prednicarbate, desonide
10. Hypnotics, sedatives
   e.g. cyclobarbital, pentobarbital, methaqualone, benzodiazepines (flurazepam, midazolam, nitrazepam, lormetazepam, flunitrazepam, triazolam, brotizolam, temazepam, loprazolam)
12. Immunotherapeutics and cytokines
   e.g. azathioprine, ciclosporin
13. Local anaesthetics
   a) internal: e.g. butanilicaine, mepivacaine, bupivacaine, etidocaine, lidocaine, articaine
   b) external also: e.g. oxybuprocaine, tetracaine, benzocaine
14. Migraine agents
   e.g. lisuride, methysergide, dihydroergotamine, ergotamine
15. Anaesthetics
   e.g. methohexital, propofol, etomidate, ketamine, thiopental, droperidol, fentanyl
16. Parathyroid hormones, calcium metabolism regulators
   e.g. dihydrotachysterol
17. Ophthalmics
   e.g. cyclodrin, cyclopentolate, homatropine, tropicamide, pholedrine, edoxudine, aciclovir, acetazolamide, diclofenamide, carteolol, timolol, metipranolol, betaxolol, pindolol, bupranolol, levobununol, carbachol
18. Psychotropics
   e.g. benzodiazepines (lorazepam, diazepam), clomethiazole
21. Sex hormones and their inhibitors
   e.g. anabolics, androgens, antiandrogens, gestagens, oestrogens, antioestrogens 22. Cytostatics and metastasis inhibitors
- a) alkylating agents, such as melphalan, carmustine, lomustine, cyclophosphamide, ifosfamide, trofosfamide, chlorambucil, busulphan, prednimustine, thiotepa
- b) antimetabolites, such as fluorouracil, methotrexate, mercaptopurine, tioguanine
- c) alkaloids, such as vinblastine, vincristine, vindesine
- d) antibiotics, such as dactinomycin
- e) taxol and related or analogous compounds
- f) dacarbazine, oestramustine, etoposide

4. EXAMPLES

The invention is explained in more detail in the following examples

Example 1

Preparation of a 3% strength nanosuspension with RMKP 22 (4-[N-(2-hydroxy-2-methylpropyl)-ethanolamine]-2.7-bis (cis-2.6-dimethylmorpholin-4-yl)-6-phenyl-pteridine)
Basic recipe:

RMKP 22 3.0

Tween 80 0.1

Aqua dest. to 100.0

The powdered drug (ground in an air jet, particles up to more than 25 μm) was rubbed in a grinding dish with a concentrated surfactant solution for wetting, and the remaining aqua dest. was then added, while stirring. Alternatively, the drug powder can also be introduced into a surfactant solution by stirring. This coarsely disperse suspension was then passed at room temperature through a continuously operating Micron LAB 40. Homogenization conditions: 1,500 bar, 1–4 cycles. The average particle diameter of the parent suspensions (=suspension with 0 cycles), measured with the laser diffractometer, and of the resulting nanosuspensions by PCS (PI=polydispersity index):

|  | Diameter | PI |
|---|---|---|
| Suspension with 0 cycle: | 3250 nm |  |
| Suspension with 2 cycles: | 406 nm | 0.244 |
| Suspension with 4 cycles: | 208 nm | 0.770 |

Basic recipe

RMKP 22 3.0

Tween 80 1.0

Aqua dest. to 100.0

Preparation as in example 1. The resulting nanosuspensions had the following PCS characteristic data:

|  | Diameter | PI |
|---|---|---|
| Suspension with 0 cycle: | 3250 nm |  |
| Suspension with 2 cycles: | 345 nm | 0.197 |
| Suspension with 4 cycles: | 242 nm | 0.188 |

Example 2

Preparation of a 9% strength nanosuspension with RMKP 22
Basic recipe

RMKP 22 9.0

Tween 80 0.3

Mannitol 16.7

Aqua dest. to 100.0

Preparation as in example 1. The resulting nanosuspensions had the following PCS characteristic data:

|  | Diameter | PI |
|---|---|---|
| Suspension with 0 cycle: | 3170 nm |  |
| Suspension with 1 cycle: | 817 nm | 0.288 |
| Suspension with 2 cycles: | 914 nm | 0.425 |
| Suspension with 3 cycles: | 646 nm | 0.395 |
| Suspension with 4 cycles: | 606 nm | 0.276 |

Example 3

Preparation of a 15% strength nanosuspension with RMKP
Basic recipe

RMKP 22 15.0

Tween 80 0.5

Mannitol 16.7

Aqua dest. to 100.0

Preparation as in example 1. The resulting nanosuspensions had the following PCS characteristic data:

|  | Diameter | PI |
|---|---|---|
| Suspension with 0 cycle: | 2880 nm |  |
| Suspension with 2 cycles: | 273 nm | 0.154 |

Example 4

Preparation of a 9% strength nanosuspension with RMKP 22/Tween 80—diameter of the nanosuspension as a function of the number of cycles:
Basic recipe

RMKP 22 9.0

Glycerol 85% 16.7

Tween 80 0.3

Aqua dest. to 100.0

Figure 4:
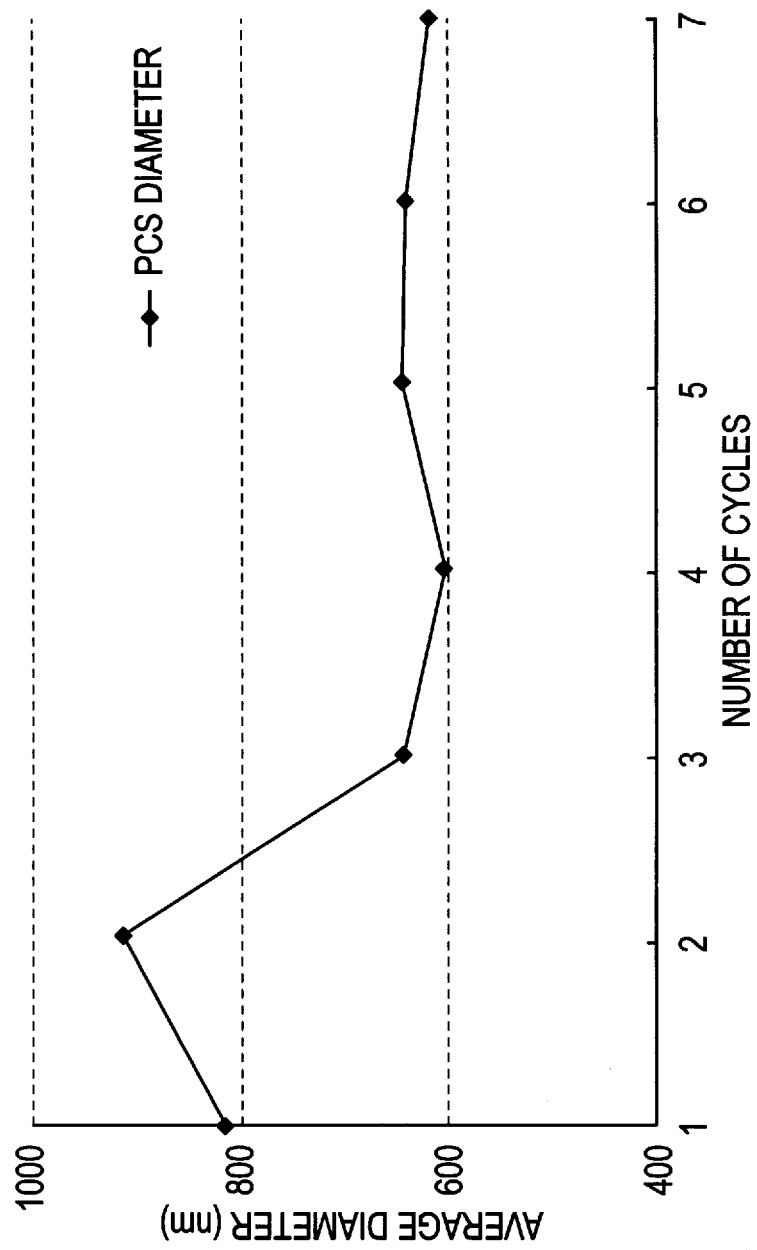
FIG. 4 illustrates a graph of the PCS diameters plotted as a function of the number of cycles.

Preparation of the suspension and subsequent homogenization as in example 1. Homogenization parameters: 1,500 bar, 1 to 7 cycles. The nanosuspension was measured by PCS. The PCS diameters are plotted as a function of the number of cycles in FIG. 4. Almost the minimum diameter of the nanosuspension of 610 nm is achieved after only approx. 3 cycles.

To evaluate the injectability of nanosuspensions, absolute particle counts per unit volume of suspension were determined with a Coulter counter (cf. example 6).

Example 5

Preparation of a 9% strength nanosuspension with RMKP 22/lecithin—diameter of the nanosuspension as a function of the number of cycles:
Basic recipe

RMKP 22 9.0

Glycerol 85% 2.5

Phospholipon 90 0.6

Aqua dest. to 100.0

Figure 5:
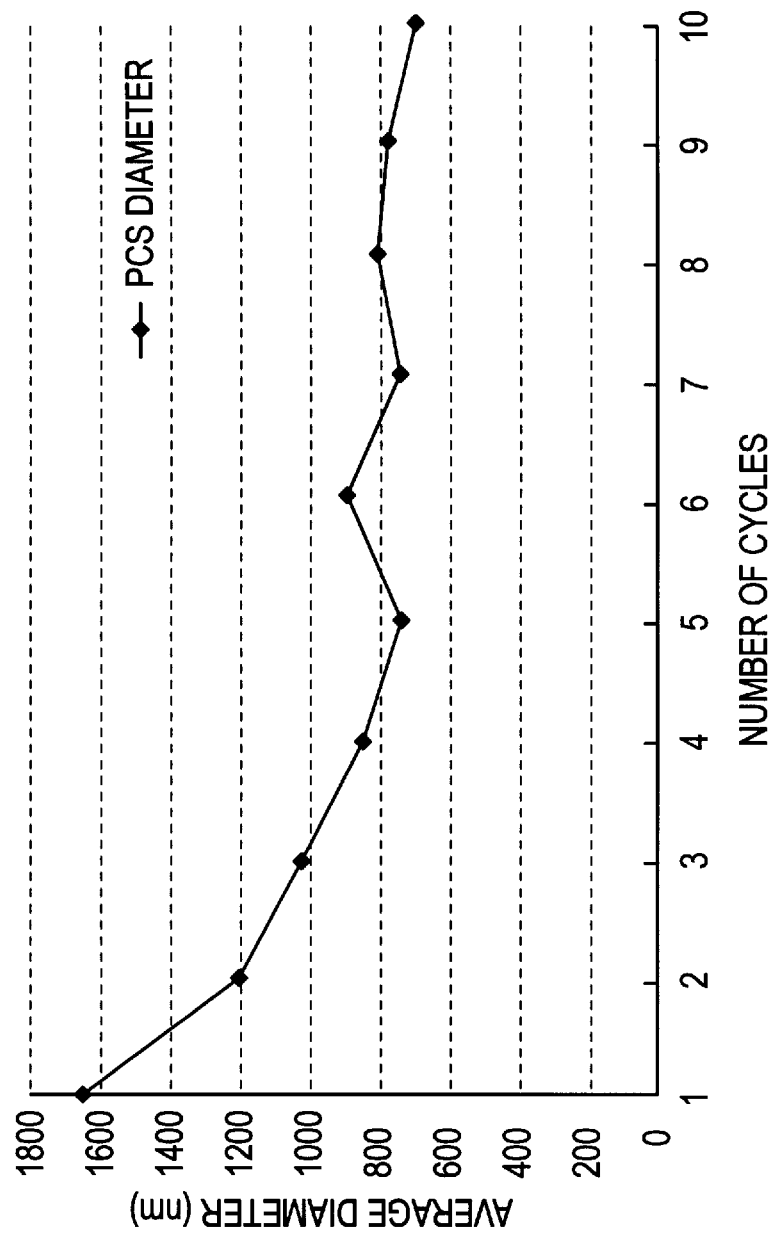
FIG. 5 illustrates a graph of the PCS diameters plotted as a function of the number of cycles.
Figure 6:
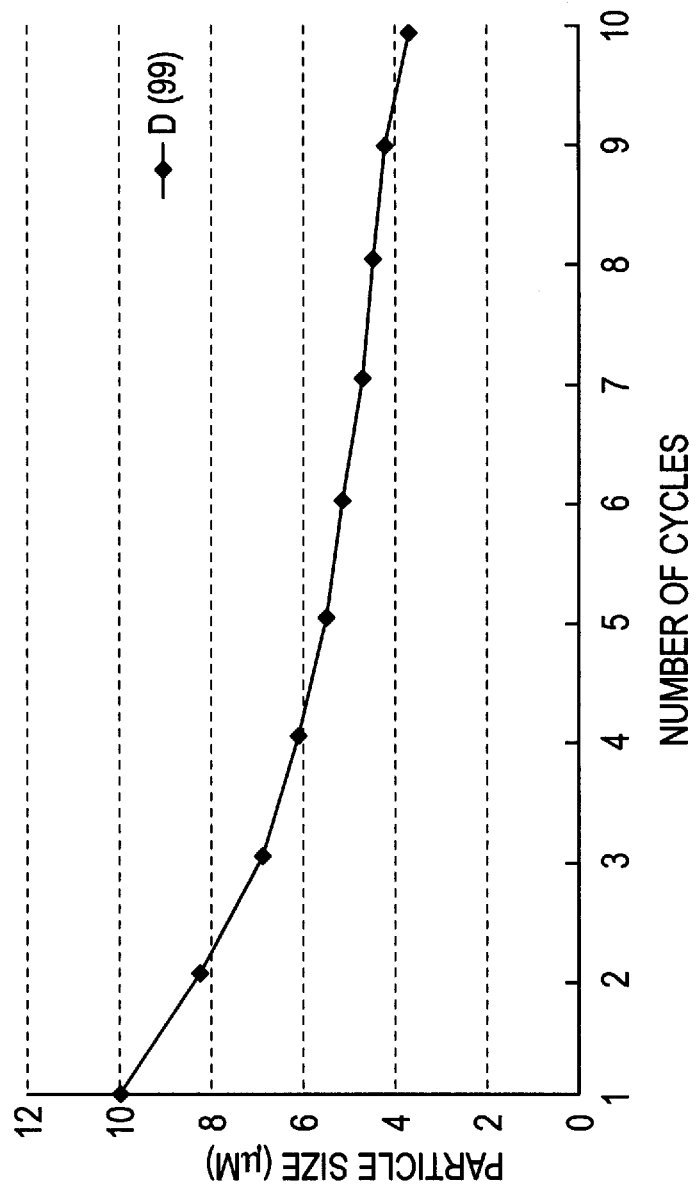
FIG. 6 illustrates a graph of the PCS diameters plotted as a function of the number of cycles.

Preparation of the suspension and subsequent homogenization as in example 1. Homogenization parameters: 1,500 bar, 1 to 10 cycles. The plot of the average PCS diameter against the number of cycles in FIG. 5 gives an almost minimum diameter of the nanosuspension after 7 cycles, 780 nm. To monitor the decrease in the particles also in the size range from 1 μm to several μm as a function of the number of cycles, the samples were analysed with the LD. The results were evaluated by plotting the 99% diameter against the number of cycles (FIG. 6). Here also, almost the minimum diameter of the nanosuspension is achieved after approx. 7 cycles. 99% diameter means that 99% of the particles are smaller than this value (volume distribution, not number distribution). This diameter is a sensitive measure for reducing the proportion of micrometer particles. After 10 cycles, the dispersity limit is also reached here, 99% of the particles are <3.87 μm, 100% are <5.29 μm.

The dispersing and grinding properties during the preparation and the particle sizes which can be achieved here are similar in Tween 80 and Phospholipon.

The laser diffractometer gives only relative distributions. To evaluate the injectability of nanosuspensions, absolute particle counts per unit volume of suspension were therefore determined with the Coulter counter (cf. example 6).

Figure 7:
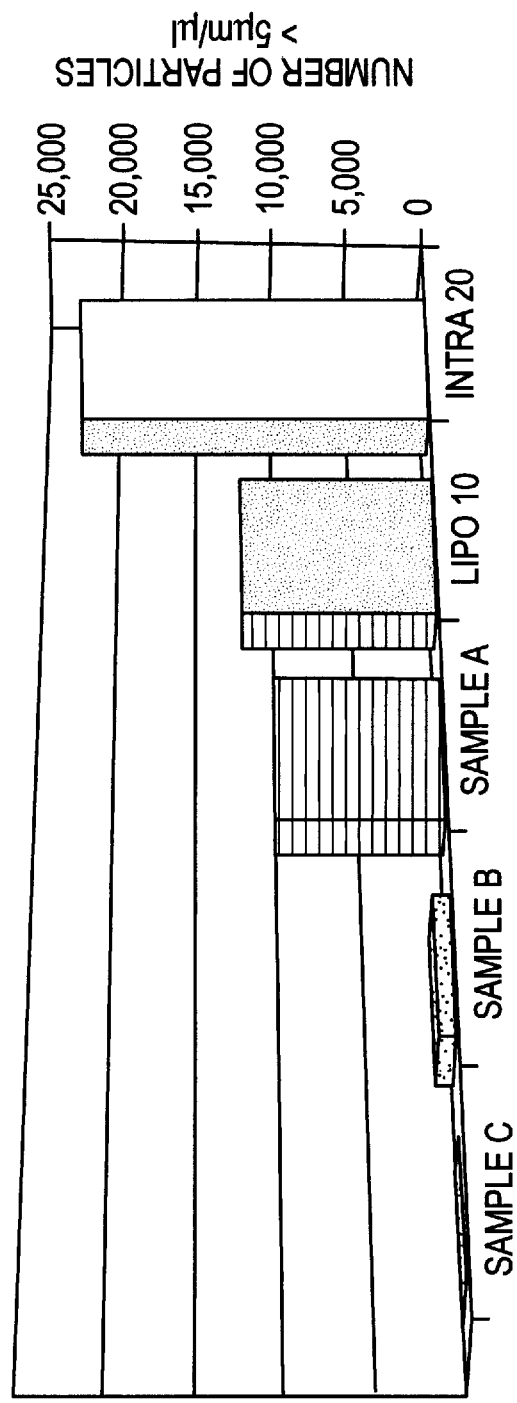
FIG. 7 illustrates a comparison of the number of particles having a diameter greater than 5 μm per μl.

Example 6
Preparation of a 9% strength nanosuspension with RMKP 22/Tween 80—proportion of particles in the micrometer range and evaluation of the i.v. injectability The laser diffractometer gives only relative distributions. To evaluate the injectability of nanosuspensions, the absolute particle counts per unit volume of suspension of the nanosuspensions prepared in example 4 were therefore determined with the Multisizer II Coulter counter. The characterizing parameter is the number of particles >5 μm per μl of nanosuspension. FIG. 7 compares the number of particles >5 μm per μl of original sample of nanosuspension A (9% RMKP 22, 0.3% Tween 80, 16.7% mannitol, aqua ad 100 wt. %, FIG. 7: sample A) and of the fat emulsions for parenteral nutrition (Lipofundin 10% and Intralipid 20%, FIG. 7: Lipo10 and Intra20). Samples in which the number of particles >5 μm had been reduced by a centrifugation step were furthermore analysed. Nanosuspension B was centrifuged at 1,559 g for 30 min, nanosuspension C was centrifuged at 3,056 g for 30 min (FIG. 7: sample B and sample C).

The number of particles in the micrometer range in the emulsions approved for i.v. infusion (infusion volume >/=500 ml p.d.) and nanosuspension A (injection volume approx. 1–20 ml) is 2.9–3.3 mg/ml. Targeted deposition of particles >5 μm by centrifugation can lower their number in nanosuspensions B and C to several times below the values of the emulsions to 1.5 mg/ml (FIG. 7: sample B and sample C, sample A centrifuged at 1,559 g and 3,056 g for 30 min.)

Figure 8:
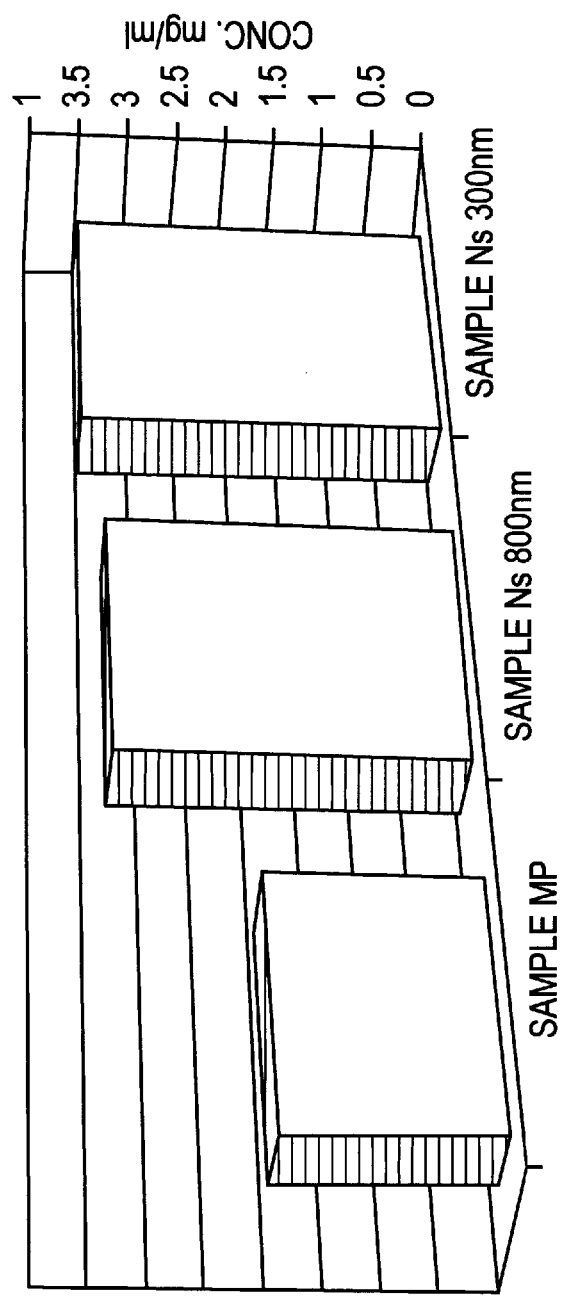
FIG. 8 illustrates a comparison of the saturation concentrations of RMKP 22 microparticles.

Example 7
Comparison of the saturation solubility of microparticles and nanosuspensions The saturation solubility Csm of the microparticles of the drug RMKP 22 which had been ground in an air jet (diameter 3.64 μm) was determined by shaking both in water and in a 0.3% strength Tween/16.7% strength aqueous mannitol solution for 7 days. After 7 days a solubility plateau was reached. An identical saturation solubility was found for both media, which rules out solubilization effects for the active compound. The saturation solubility Csn in two RMKP 22 nanosuspensions (diameter 800 nm and 300 nm) was determined in the dispersion medium (Tween 80/mannitol solution) after the solid phase had been centrifuged off. FIG. 8 compares the saturation concentrations of RMKP 22 microparticles which have been ground in an air jet (sample MP, diameter 2.40 μm) and of two RMKP 22 nanosuspensions (sample NS 800 nm, sample NS 300 nm, average diameter: 800 and 300 nm). The saturation solubility Csm of the microparticles is 1.97 mg/l and is achieved only after shaking for three days. This means that the medicament dissolves very slowly. No significant difference was detected between the saturation solubilities of the two powders. The saturation solubility of the nanosuspension was determined analogously 7 days after preparation, and gave values of 3.29 mg/l and 3.52 mg/l. An increase in the saturation solubility with decreasing particle size is described in the Ostwald-Freundlich equation, where the values measured are attributed not only to a mere increase in the surface area.

Example 8
Dissolution properties of nanosuspensions compared with microparticles
Nanosuspension basic recipe
RMKP 22 9.0
Tween 80 0.3
Mannitol 16.7
Aqua dest. to 100

Dissolution of particles can be determined with a Coulter counter. After introduction of a few μl of particle suspension into the measurement volume of 100 ml, in the case of a soluble substance the particles dissolve in the course of three successive repeat measurements, the volume distribution curve decreasing from measurement 1 to 3. To prevent dissolution processes, measurements are made in an NaCl solution saturated with substance in the case of such substances.

To prepare a solution saturated with drug, excess drug which had been ground in an air jet was added to the 0.9% NaCl solution and the saturation solubility of the microparticles Csm was reached by shaking. The saturated drug solution was prepared specifically not with coarsely crystalline drug but with drug microparticles, so that the higher saturation concentration also establishes saturation solubility over this finely disperse system in accordance with the Ostwald-Freundlich equation.

Figure 9:
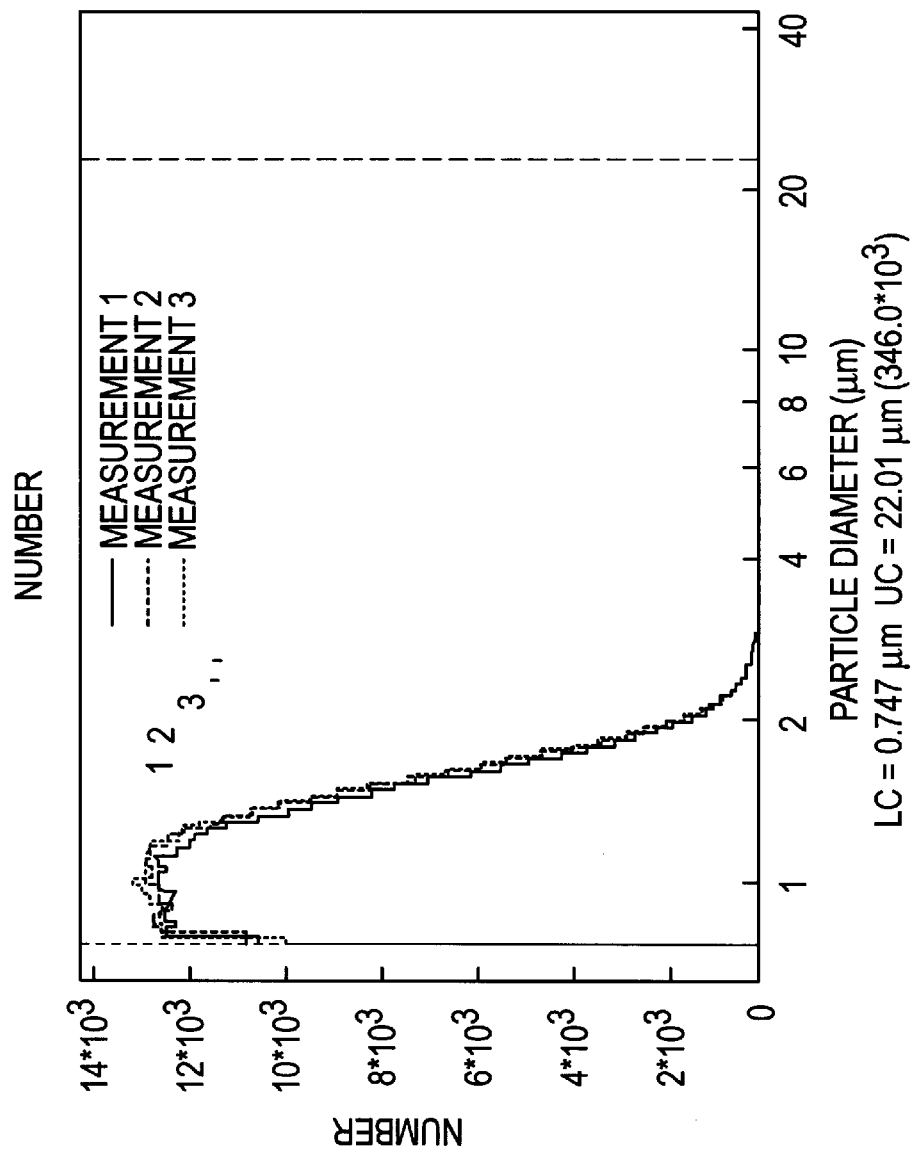
FIG. 9 illustrates a volume distribution curve of RMKP 22.

Introduction of RMKP 22 drug particles which had been ground in an air jet, i.e. particles with a diameter of 3.64 μm into this 0.9% NaCl solution saturated with drug accordingly led to no solution phenomena at all within the measurement time of approx. 10 minutes (three repeat measurements of 150 s at intervals of 100 s), the three measurement curves obtained in succession being congruent (FIG. 9). The total volume of the particles of a sample is 393,000 μm$^3$ during the first measurement, 391,400 μm$^3$ during the second measurement and then 386,500 μm$^3$ (FIG. 9). The total volume of the particles remains constant over the period of the measurement cycle.

Figure 10:
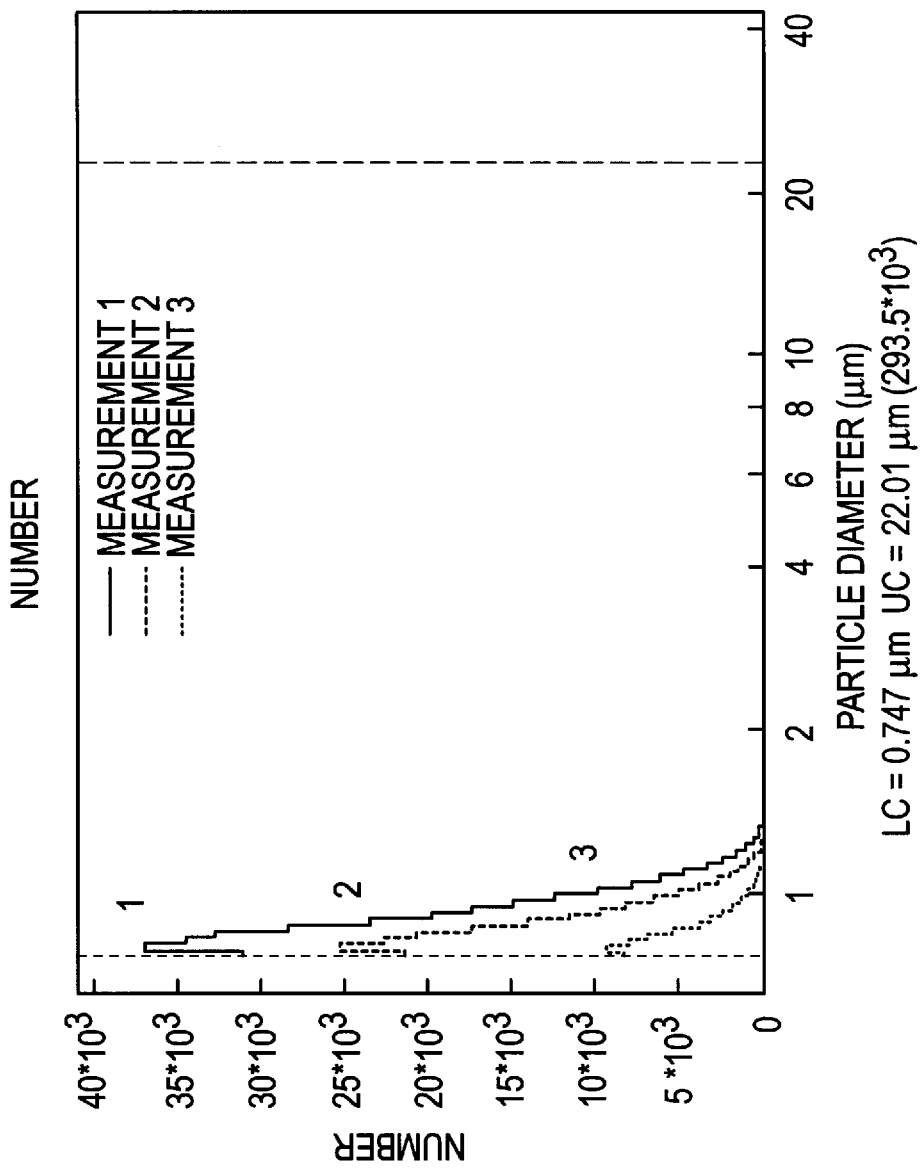
FIG. 10 illustrates a volume distribution curve of RMKP 22.

Measurement of the nanosuspension, i.e. particles in the nanometer size, led—in spite of 0.9% NaCl solution saturated with drug—to dissolution of the particles within the measurement time of approx. 10 min, 65% of the particles dissolving. The Coulter counter volume distribution of the nanosuspension at the three successive measurements (start of measurement at times: T=0 s, T =450 s, T =1,100 s, duration of one measurement: 150 s) gives a total volume of the particles of 121,000 μm$^3$ during the first measurement, 83,762 μm$^3$ during the second measurement and a value of 42,038 μm$^3$ during the third measurement (FIG. 10). The decreasing area under the volume distribution curve is a measure of the dissolution of the nanosuspension.

A decrease in the total volume of the particles of a sample observed over the period of a Coulter counter measurement cycle documents the dissolution properties of the nanoparticles in the measurement medium chosen and shows the constant behaviour of the micronized particles in the same measurement medium.

Example 9
Long-term stability of nanosuspensions
Basic recipes
  A. 9% RMKP 22, 0.3% Tween 80, 16.7% mannitol, aqua dest. to 100%
  B. 9% RMKP 22, 1% Tween 80, 16.7% mannitol, aqua dest. to 100%
  C. 9% RMKP 22, 0.6% Phospholipon 90%, aqua dest. to 100%

The recipes were prepared as described in example 1, homogenization parameters: 1,500 bar, 10 cycles. Analysis by PCS (main diameter) and with the laser diffractometer (99% and 95% diameter).

The PCS diameters and the associated polydispersity indices of the nanosuspensions stored were:
  Batch A 740 nm 0.259
  Batch B 719 nm 0.282
  Batch C 286 nm 0.310

Figure 11:
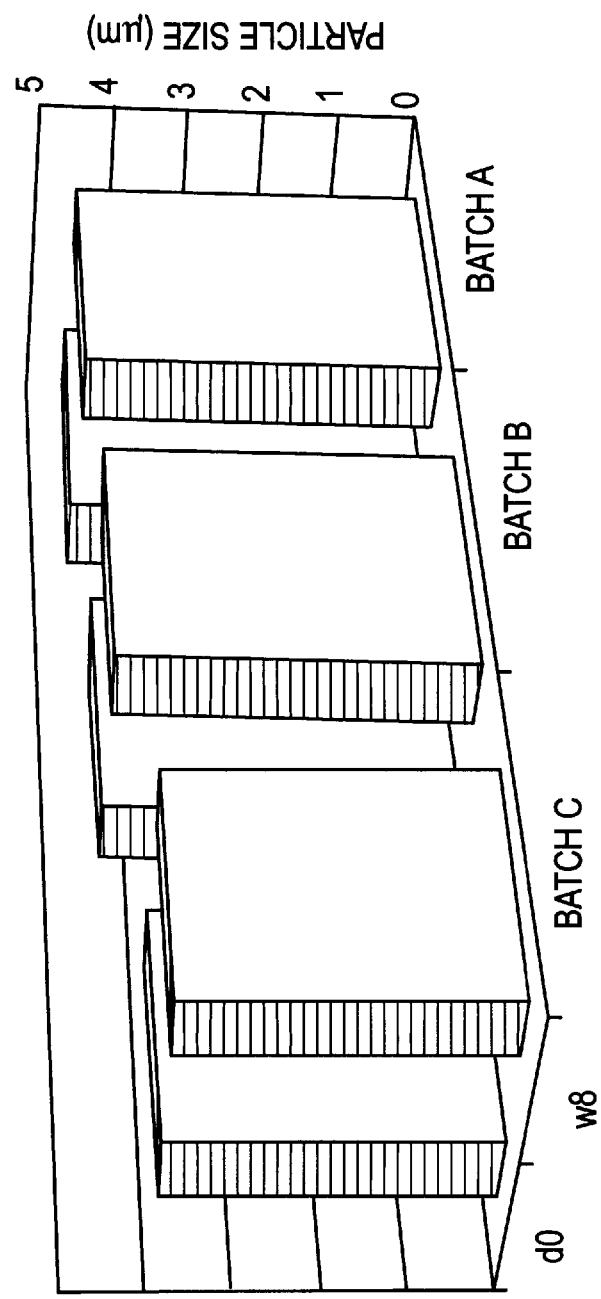
FIG. 11 illustrates a change in particle size over time.
Figure 12:
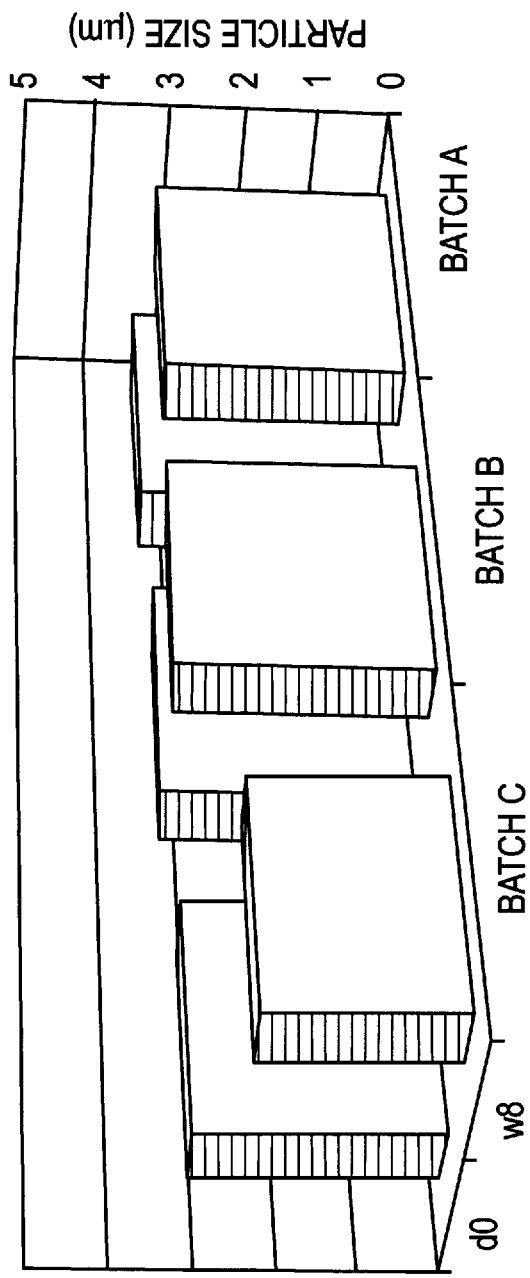
FIG. 12 illustrates a change in particle size over time.

The diameters and polydispersity indices showed no significant change in the particle size distribution during the storage period. The 99% (FIG. 11) and 95% (FIG. 12) LD diameters of nanosuspensions A, B and C also remain constant over a storage period of 8 weeks (w8), compared with the diameters on the day of preparation d0).

Example 10
Stability of nanosuspensions during sterilization: autoclaving A121
  Composition of parent suspension A:
3% RMKP 22, 0.3% Tween 80, 16.7% mannitol, aqua dest. ad to 100 wt. %.

Figure 13:
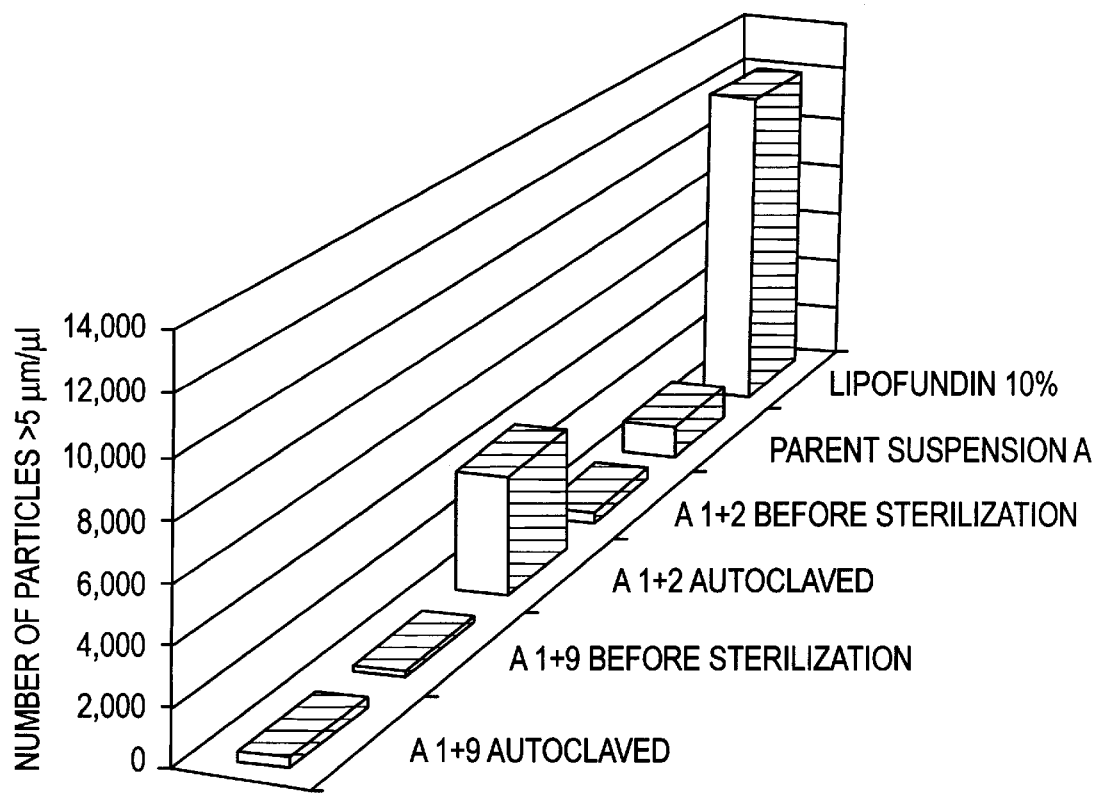
FIG. 13 illustrates the number of particles greater than 5 μm per μl before and after sterilization.

For sterilization, parent suspension A was diluted with aqua dest. to medicament use concentrations, and therefore to the surfactant concentrations of 1% (FIG. 13: Al+2) and to 0.3% (FIG. 13: Al+9). Sterilization was carried out with pressurized steam in an autoclave in accordance with German Pharmacopoeia, 10th edition (15 minutes, 121° C. under 2 bar). The particles were analysed with the Coulter counter and by PCS.

FIG. 13 shows the Coulter counter results of parent suspension A (FIG. 13: parent suspension A), of nanosuspensions A 1+2 and A 1+9 before sterilization (FIG. 13: A 1+2/9, before sterilization) and after sterilization (FIG. 13: A 1+2/+9, autoclaved). The number of particles >5 µm per µl in Lipofundin 10% (FIG. 13: Lipofundin 10%) have been used as a comparison. PCS data give the main particle diameter of parent suspension A and the main diameters of nanosuspensions A 1+2 and A 1+9 after autoclaving (FIG. 14: A 1+2 /+9, autoclaved).

Figure 14:
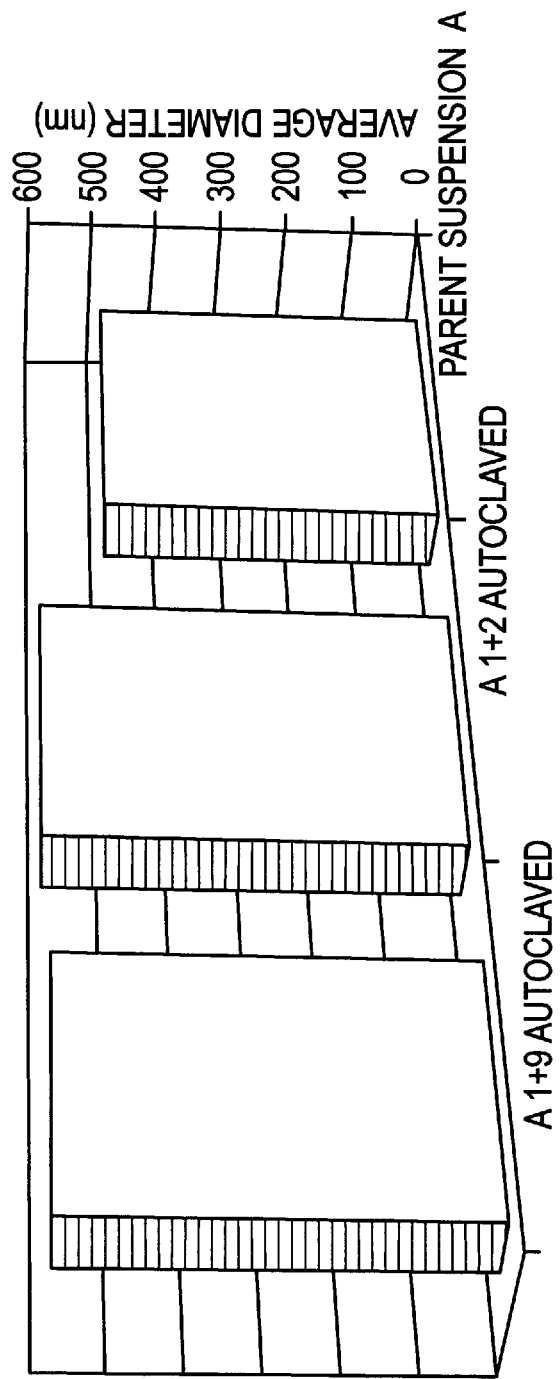
FIG. 14 illustrates the particle diameter before and after sterilization.

The number of particles greater than 5 µm rose as a result of exposure of the nanosuspensions to heat and the resulting formation of aggregates. In nanosuspension A 1+2, diluted with 2 parts of water, the number of particles >5 µm increased above the value of the more highly concentrated, non-sterilized parent suspension A, but still remained significantly below the values of the fat emulsions. Dilution with 9 parts of water lowered the probability of collision of two particles due to the reduction in the particle concentration so greatly that a significant increase in the number of particles before and after sterilization was no longer detectable. The diameters increased during autoclaving by 98 nm and 91 nm (A 1+2/A 1+9), which does not impair i.v. injectability (FIG. 14).

Example 11
Stability of nanosuspensions during sterilization: gamma sterilization
  Composition of nanosuspensions A and B:
Nanosuspension A: 2% RMKP, 0.3% Tween 80, 16.7% mannitol, aqua dest. to 100 wt. %.
Nanosuspension B: 3% RMKP, 0.3% Tween 80, 16.7% mannitol, aqua dest. to 100 wt. %.

Nanosuspensions A and B were sterilized with a cobalt-60 source at a dose of 2.5 Mrad (25 kGray). Analysis was carried out with the Multisizer II Coulter counter and by PCS.

Figure 15:
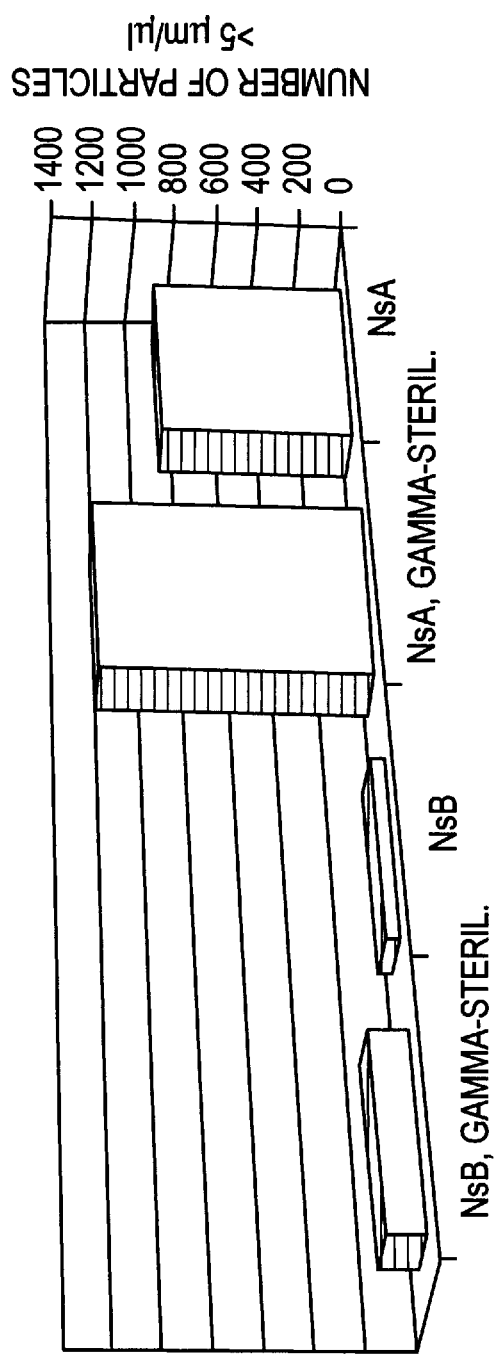
FIG. 15 illustrates the number of particles greater than 5 μm per μl before and after sterilization.
Figure 16:
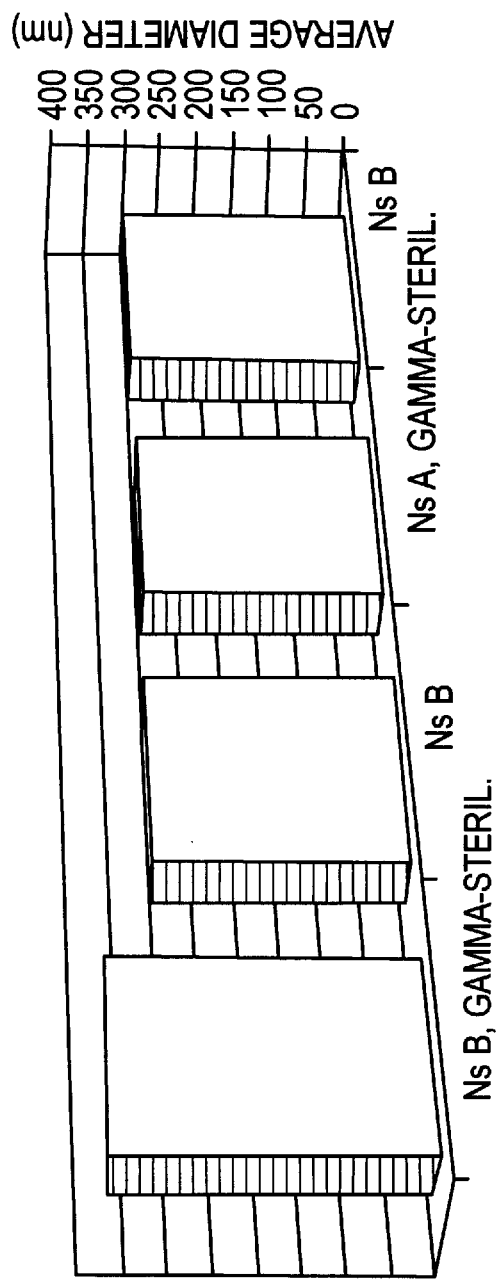
FIG. 16 illustrates the particle diameter before and after sterilization.

The number of particles >5 µm per µl of nanosuspensions A and B before sterilization and after sterilization (FIG. 15: Ns A, Ns B/Ns A, gamma-steril., Ns B, gamma-steril.) are recorded with the Coulter counter (FIG. 15). The particle counts in Lipofundin 10% and Intralipid 20% serve as a comparison:
  12,176 and 22,525 particles >5 µm per µl of emulsion The PCS particle diameters of nanosuspensions A and B before (NS A/NS B) and after sterilization (NS A, gamma-steril., NS B, gamma-steril.) are shown in FIG. 16.

There was a moderate increase in the particles >5 µm during sterilization, in nanosuspension A from 890 to 1,222 and in nanosuspension B from 60 to 165, the numbers still remaining significantly below the values in the fat emulsion even after the sterilization. The PCS diameter does not increase in nanosuspension A (303 nm before, 299 after sterilization) and increases slightly in nanosuspension B (from 306 to 367 nm). The particle diameters in parenteral fat emulsions vary in the range from approx. 200 to 400 nm.

Figure 17:
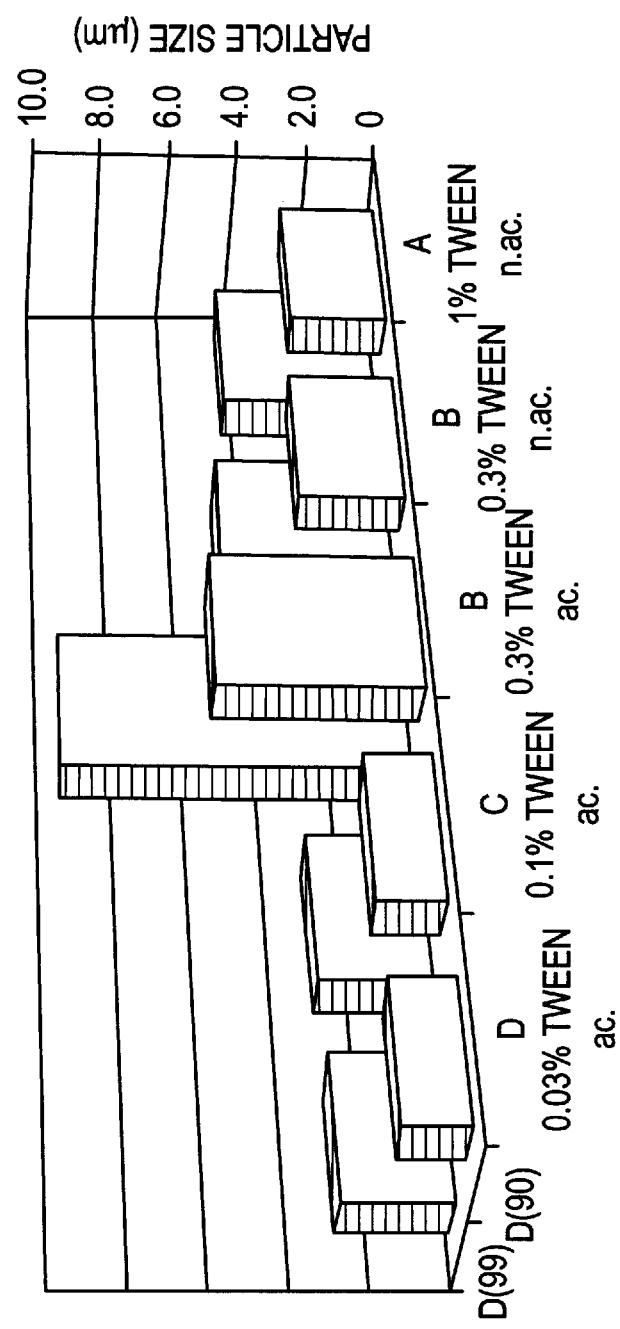
FIG. 17 illustrates a change in particle size over time.

Example 12
Stability of nanosuspensions during sterilization as a function of the surfactant concentration Nanosuspensions of RMKP stabilized with various Tween 80 concentrations, were sterilized with A121 and analysed in respect of particle growth with the laser diffractometer (FIG. 17).

Composition of the nanosuspensions:
  A. 1.0% Tween, 9% RMKP, mannitol 16.7%
  B. 0.30% Tween, 9% RMKP, mannitol 16.7%
  C. 0.10% Tween, 0.9% RMKP, mannitol 16.7%
  D. 0.03% Tween, 0.9% RMKP, mannitol 16.7%

The recipes each comprised aqua dest. to 100 wt. %, and nanosuspensions C and D were prepared from parent suspension B by dilution to the use concentration. Tween 80 was added to nanosuspension C after the dilution to adjust it to 0.10%.

The 99% and 90% LD diameters of nanosuspensions with different Tween 80 concentrations before and after autoclaving serve as characterizing parameters for the particle growth (FIG. 17: n. ac./ac.). Data from nanosuspension B (FIG. 17: B, 0.3% Tween 80 n.ac.) are the starting values for suspensions C and D before autoclaving (FIG. 17).

The nanosuspension with 1% Tween 80 already showed macroscopic visible aggregates after autoclaving, and was therefore no longer analysed by means of the laser diffractometer. Surprisingly, the nanosuspensions showed a higher stability with decreasing surfactant concentration.

Example 13
Surfactant-free nanosuspensions with carbamazepine
Basic recipe

Carbamazepine 1.0

Sodium carboxymethylcellulose 0.1

Aqua dest. to 100.0

Sodium carboxymethylcellulose was dissolved in water and the powdered active compound was rubbed with this solution in a grinding dish. The batch was dispersed in an Ultraturrax for 2 min. This coarse predispersion was then homogenized under 1,500 bar over 5 cycles.
Characteristic data of the nanosuspension 436 nm diameter 0.263 polydispersity index

Example 14
Tetracaine nanosuspension prepared with shearing and impact dispersion (jet stream)
Basic recipe Tetracaine Base 1.0

Lecithin S 75 0.3

Pluronic F68 2.2

Glycerol 85% 2.2

Aqua dest. to 100.0

Tetracaine base is rubbed with the Pluronic solution and then passed under a pressure of 600 bar in 5 cycles through the Microfluidizer model 110-Y (Microfluidics Inc.). A nanosuspension was also obtained with this dispersing principle.
Characteristic data of the nanosuspension 379 nm diameter 0.529 polydispersity index

Example 15
Tetracaine nanosuspension <100 nm prepared with cavitation
Basic recipe Tetracaine base 1.0

Pluronic F68 2.2

Lecithin S75 0.3

Glycerol 85% 2.2

Aqua dest. to 100.0

The preparation was carried out as described in example 1, homogenization parameters: 1,500 bar and 10 cycles. The analysis was carried out by PCS.
Characteristic data of the nanosuspension 91 nm diameter 0.489 polydispersity index Because of the special composition of the recipe (low concentration of the disperse phase), nanosuspensions with a particle size below 100 nm were obtained, these being a potential system for targeting, e.g. to endothelial cells of the blood capillaries (particles are internalized here by pinocytosis, which is limited to particles <150 nm).

Example 16
Prednisolone nanosuspension <100 nm prepared with cavitation
Basic recipe Prednisolone 1.0

Pluronic F68 2.2

Lecithin S75 0.3

Glycerol 85% 2.2

Aqua dest. to 100.0

The preparation was carried out as described in example 1, homogenization parameters: 1,500 bar and 10 cycles. The analysis was carried out by PCS and with the laser diffractometer (LD).
Characteristic data of the nanosuspension 897 nm diameter 0.040 polydispersity index 3.80 95% diameter (LD)

4.74 μm 99% diameter (LD)

We claim:

1. Drug carrier comprising particles of at least one therapeutically active compound which is insoluble, only sparingly soluble or moderately soluble in water, aqueous media and/or organic solvents, wherein said active ingredient is solid at room temperature and has an average diameter, determined by photon correlation spectroscopy (PCS) of 10 nm to 1,000 nm, the proportion of particles larger than 5 μm in the total population being less than 0.1% (number distribution determined with a Coulter counter), and, when introduced into water, aqueous media and/or organic solvents, the active compound has an increased saturation solubility and an increased rate of dissolution compared with powders of the active compound prepared using an ultrasonic probe, a ball mill or a pearl mill, the solid particles having been comminuted, without prior conversion into a melt, by using a piston-gap homogenizer.

2. Carrier according to claim 1, wherein the particles of the main population have an average diameter of between 40 and 1,000 nm.

3. Carrier according to claim 1, wherein said carrier is prepared using the jet stream principle.

4. Carrier according to claim 1, wherein said carrier is prepared using synthetic, semi-synthetic or naturally occurring surfactants in concentrations of 0.001–30%.

5. Carrier according to claim 1, wherein said carrier is prepared with exclusion of the use of organic solvents.

6. Carrier according to claim 1, wherein said carrier is prepared without the use of ultrasonic probes or ball or pearl mills.

7. Carrier according to claim 1, wherein the proportion of the internal or drug phase, based on the total weight of said carrier, is 0.1 to 30 wt. %.

8. Carrier according to claim 1, wherein the drug carrier comprises an active compound or active compounds which are slightly soluble or insoluble in water or aqueous solutions.

9. Carrier according to claim 1, wherein the drug carrier comprises an active compound or active compounds which are slightly soluble or insoluble in organic solvents.

10. Carrier according to claim 1, wherein the drug carrier comprises an active compound or active compounds which are slightly soluble or insoluble in water or aqueous solutions and in organic solvents.

11. Carrier according to claim 1, wherein the drug carrier comprises an active compound or active compounds which have a moderate solubility in water or aqueous solutions and/or in organic solvents.

12. Carrier according to claim 1, wherein said carrier comprises one or more dispersion-stabilizing substances.

13. Carrier according to claim 12, wherein said carrier comprises the dispersion-stabilizing substances in an amount of 0.001 to 20 wt. %, based on the total weight of said carrier.

14. Carrier according to claim 12, wherein the dispersion-stabilizing substances are compounds from the series consisting of poloxamers, poloxamines, ethoxylated mono-and diglycerides, ethoxylated lipids and lipoids, ethoxylated fatty alcohols and alkylphenols, ethoxylated fatty acid esters, polyglycerol ethers and esters, lecithins, esters and ethers of sugars or sugar alcohols with fatty acids or fatty alcohols, phospholipids and sphingolipids, sterols, esters or ethers thereof and mixtures of these compounds.

15. Carrier according to claim 12, wherein the stabilizing substance comprises egg lecithin, soya lecithin or hydrogenated lecithin, mixtures thereof or mixtures of one or both lecithins with one or more phospholipid components, cholesterol, cholesterol palmitate, or stigmasterol.

16. Carrier according to claim 1, further comprising charge stabilizers.

17. Carrier according to claim 16, further comprising charge stabilizers in an amount of 0.01 to 20 wt. %, based on the total weight of said carrier.

18. Carrier according to claim 16, wherein the charge stabilizers comprise dicetyl phosphate, phosphatidylglycerol, saturated or unsaturated fatty acids, sodium cholate, anti-flocculants or amino acids.

19. Carrier according to claim 1, further comprising one or more viscosity-increasing substances.

20. Carrier according to claim 19, further comprising viscosity-increasing substances in an amount of 0.1 to 20 wt. %, based on the total weight of said carrier.

21. Carrier according to claim 19 wherein the viscosity-increasing substances comprises cellulose ethers and esters, polyvinyl alcohol, alginates, xanthans, pectins, polyacrylates, poloxamers and poloxamines.

22. Carrier according to claim 19, further comprising a compound selected from the group consisting of sugars or sugar alcohols, glucose, mannose, trehalose, mannitol and sorbitol.

23. Carrier according to claim 19, further comprising charge carriers.

24. Carrier according to claim 1, characterized in that the particles are dispersed in distilled water or an aqueous medium or in an aqueous medium with additions of electrolytes, mono- and disaccharides, polyols or mixtures thereof.

25. Carrier according to claim 24, wherein the additions comprise sodium chloride, mannose, glucose, fructose, xylose, mannitol, sorbitol, xylitol and glycerol.

26. Carrier according to claim 1, wherein the particles are lyophilized or spray dried.

27. Carrier according to claim 1, further comprising one or several active compounds.

28. Carrier according to claim 27, wherein, in the case of several active compounds, one active compound or several active compounds are dissolved or dispersed in another or several others, adsorbed onto the surface thereof or dispersed as a solution in the particle.

29. Carrier according to claim 1, wherein said particles are dispersed in a non-aqueous medium.

30. Carrier according to claim 29, wherein said particles are dispersed in a liquid, semisolid or solid medium.

31. Carrier according to claim 30, wherein said particles are dispersed in a liquid oily medium.

32. Carrier according to claim 30, wherein the medium comprises lipids or lipoids or mixtures thereof.

33. Carrier according to claim 32, wherein the medium comprises mono-, di- or triglycerides, waxes, fatty alcohols and fatty alcohol esters, beeswax, oleyl oleate, isopropyl myristate, wool fat or mixtures thereof.

34. Carrier according to claim 30, wherein the medium comprises longer-chain organic molecules or polymers, of liquid, semisolid or solid polyethylene glycols, poloxamers, poloxamines or mixtures thereof.

35. Process for the preparation of the drug carrier according to claim 1, wherein it is produced by using cavitation, wherein the drug or the drug mixture is ground to a powder, dispersed in a dispersing agent and forced under pressure through a gap, where cavitation occurs.

36. Process for the preparation of the drug carrier according to claim 1, wherein it is produced by using shearing and impact forces, wherein the drug or the drug mixture is ground to a powder, dispersed in a dispersing agent and then ground in the wet state, in particular in a jet stream system.

37. Drug carrier comprising particles of at least one therapeutically active compound which is insoluble, only sparingly soluble or moderately soluble in water, aqueous media and/or organic solvents, wherein said active ingredient is solid at room temperature and has an average diameter, determined by photon correlation spectroscopy (PCS) of 40 nm to 100 nm, the proportion of particles larger than 5 $\mu$m in the total population being less than 0.1% (number distribution determined with a Coulter counter), the solid particles having been comminuted, without prior conversion into a melt, by using a piston-gap homogenizer.

38. A method of making a drug carrier comprising the steps of:
   subjecting at least one solid therapeutically active compound dispersed in a solvent to high pressure homogenization in a piston-gap homogenizer to form particles having an average diameter, determined by photon correlation spectroscopy (PCS) of 40 nm to 100 nm, the proportion of particles larger than 5 $\mu$m in the total population being less than 0.1% (number distribution determined with a Coulter counter), without prior conversion into a melt, wherein said active compound is solid at room temperature and is insoluble, only sparingly soluble or moderately soluble in water, aqueous media and/or organic solvents.

39. Drug carrier comprising particles of at least one therapeutically active compound which is insoluble, only sparingly soluble or moderately soluble in water, aqueous media and/or organic solvents, wherein said active ingredient is solid at room temperature and has an average diameter, determined by photon correlation spectroscopy (PCS) of 10 nm to 1,000 nm, the proportion of particles larger than 5 $\mu$m in the total population being less than 0.1% (number distribution determined with a Coulter counter), and, when introduced into water, aqueous media and/or organic solvents, the active compound has an increased saturation solubility and an increased rate of dissolution compared with powders of the active compound prepared using an ultrasonic probe, a ball mill or a pearl mill, the solid particles having been comminuted, without prior conversion into a melt, by using cavitation or shearing and impact forces with introduction of a high amount of energy, and wherein said active compound comprises at least one compound selected from the group consisting of:
   analgesics, anaesthetics, antirheumatics, antiallergics, antibiotics, antiepileptics, antimycotics, calcium metabolism regulators, chemotherapeutics, corticoids, cytokines, cytostatics, dermatics, hypnotics, immunotherapeutics, local anesthetics, metastasis inhibitors, migraine agents, ophthalmics, parathyroid hormones, psychotropics, sedatives, and sex hormones.

40. A drug carrier according to claim 39, wherein said active compound comprises an analgesic selected from the group consisting of morphine, codeine, piritramide, fentanyl, levomethadone, tramadol, diclofenac, ibuprofen, indomethacin, naproxen, and prioxicam.

41. A drug carrier according to claim 39, wherein said active compound comprises an antiallergic selected from the group consisting of pheniramine, dimethindene, terfenadine, astemizole, loratidine, dosylamine and meclozine.

42. A drug carrier according to claim 39, wherein said active compound comprises an antibiotic selected from the group consisting of rifampicin, ethambutol and thiacetazone.

43. A drug carrier according to claim 39, wherein said active compound comprises an antiepileptic selected from the group consisting of clonazepam, mesuximide, phenyltoin, and valproic acid.

44. A drug carrier according to claim 39, wherein said active compound comprises an antimycotic selected from the group consisting of natamycin, amphotericin B, miconazole, clotrimazole, econazole, fenticonazole, bifonazole, ketoconazole and tolnaftate.

45. A drug carrier according to claim 39, wherein said active compound comprises a corticoide selected from the group consisting of aldosterone, fludrocortisone, betamethasone, dexamethasone, triamcinolone, fluocortolone, hydroxycortisone, prednisolone, prednylidene, cloprednol and methylprednisolone.

46. A drug carrier according to claim 39, wherein said active compound comprises a dermatic selected from the group consisting of tetracycline, erythromycin, framyctin, tyrothricin, fusidic acid, vidarabine, amcinonide, fluprednidene, alclometasone, clobetasol, diflorasone, halcinonide, fluocinolone, clocortolone, flumethasone, diflucortolone, fludroxycortide, halmethasone, desocimetasone, fluoconolide, fluocortin butyl, fluprendidene, prednicarbate, and desonide.

47. A drug carrier according to claim 39, wherein said active compound comprises a hypnotic selected from the group consisting of cyclobarbital, pentobarbital, methaqualone and benzodiazepines.

48. A drug carrier according to claim 39, wherein said active compound comprises an immunotherapeutic selected from the group consisting of azathioprine and ciclosporin.

49. A drug carrier according to claim 39, wherein said active compound comprises a local anaesthetic selected from the group consisting of butanilicaine, mepivacaine, bupivacaine, etidocaine, lidocaine, articaine, oxybuprocaine, tetracaine, and benzocaine.

50. A drug carrier according to claim 39, wherein said active compound comprises a migraine agent selected from the group consisting of lisuride, methysergide, dihydroergotamine, and ergotamine.

51. A drug carrier according to claim 39, wherein said active compound comprises an anaesthetic selected from the group consisting of methohexital, propfol, etomidate, ketamine, thiopental, droperidol and fentanyl.

52. A drug carrier according to claim 39, wherein said active compound comprises dihydrotachysterol.

53. A drug carrier according to claim 39, wherein said active compound comprises an ophthalmic selected from the group consisting of cyclodrin, cyclopntolate, homatropine, trompcamide, pholedrine, edoxudine, aciclovir, acetazolamide, diclofenamide, carteolol, timolol, metipranolol, betaxolol, pindolol, bupranolol, levobununol, and carbachol.

54. A drug carrier according to claim 39, wherein said active compound comprises a psychotropic selected from the group consisting of benzodiazepines.

55. A drug carrier according to claim 39, wherein said active compound comprises a sex hormone selected from the group consisting of anabolics, androgens, antiandrogens, gestagens, oestrogens and antioestrogens.

56. A drug carrier according to claim 39, wherein said active compound comprises a cytostatic or metastasis inhibitor selected from the group consisting of alkylating agents, antimetabolites, alkaloids, antibiotics, taxol and decarbazine.

57. A method of making a drug carrier comprising the steps of:
    subjecting at least one solid therapeutically active compound dispersed in a solvent to high pressure homogenization in a piston-gap homogenizer to form particles having an average diameter, determined by photon correlation spectroscopy (PCS) of 40 nm to 100 nm, the proportion of particles larger than 5 $\mu$m in the total population being less than 0.1% (number distribution determined with a Coulter counter), without prior conversion into a melt, wherein said active compound is solid at room temperature and is insoluble, only sparingly soluble or moderately soluble in water, aqueous media and/or organic solvents, wherein said active compound comprises at least one compound selected from the group consisting of:
    analgesics, anaesthetics, antirheumatics, antiallergics, antibiotics, antiepileptics, antimycotics, calcium metabolism regulators, chemotherapeutics, corticoids, cytokines, cytostatics, dermatics, hypnotics, immunotherapeutics, local anesthetics, metastasis inhibitors, migraine agents, ophthalmics, parathyroid hormones, psychotropics, sedatives, and sex hormones.

* * * * *